US006984383B1

(12) United States Patent
Co et al.

(10) Patent No.: US 6,984,383 B1
(45) Date of Patent: Jan. 10, 2006

(54) METHOD OF TRANSPLANTING CELLS BY CONTACTING DONOR CELLS WITH B7-1-AND B7-2-SPECIFIC IMMUNOGLOBULINS

(75) Inventors: Man Sung Co, Cupertino, CA (US); Maximiliano Vasquez, Palo Alto, CA (US); Beatriz Carreno, Acton, MA (US); Abbie Cheryl Celniker, Newton, MA (US); Mary Collins, Natick, MA (US); Samuel Goldman, Acton, MA (US); Gary S. Gray, Brookline, MA (US); Andrea Knight, Hampton, NH (US); Denise O'Hara, Reading, MA (US); Bonita Rup, Reading, MA (US); Geertruida M. Veldman, Sudbury, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 09/626,731

(22) Filed: Jul. 27, 2000

Related U.S. Application Data

(62) Division of application No. 09/249,011, filed on Feb. 12, 1999.

(51) Int. Cl.
*A61K 39/395* (2006.01)
*A61K 35/26* (2006.01)
*A61K 35/28* (2006.01)
*C07K 16/28* (2006.01)

(52) U.S. Cl. .............................. 424/153.1; 424/130.1; 424/133.1; 424/140.1; 424/141.1; 424/143.1; 424/144.1; 424/173.1; 424/93.7; 424/93.71; 424/577; 424/578; 530/387.1; 530/387.3; 530/388.1; 530/388.2; 530/388.22; 530/388.7; 530/388.73

(58) Field of Classification Search ............. 424/130.1, 424/133.1, 143.1, 173.1, 577; 530/387.1, 530/388.2, 388.73
See application file for complete search history.

(56) References Cited

U.S. PATENT DOCUMENTS

| | | | |
|---|---|---|---|
| 5,397,703 A | 3/1995 | de Boer et al. .......... | 435/172.2 |
| 5,562,903 A | 10/1996 | Co et al. ................. | 424/133.1 |
| 5,585,089 A | 12/1996 | Queen et al. ............ | 424/133.1 |
| 5,622,701 A | 4/1997 | Berg ....................... | 424/153.1 |
| 5,624,821 A | 4/1997 | Winter et al. ............. | 435/69.6 |
| 5,648,260 A | 7/1997 | Winter et al. ............ | 435/252.3 |
| 5,693,762 A | 12/1997 | Queen et al. ............ | 530/387.3 |
| 5,747,034 A | 5/1998 | de Boer et al. .......... | 424/137.1 |
| 5,869,050 A | 2/1999 | de Boer et al. .......... | 424/156.1 |
| 5,919,449 A * | 7/1999 | Dinsmore | |
| 6,084,067 A | 7/2000 | Freeman et al. ........... | 530/350 |
| 6,096,537 A * | 8/2000 | Chappel | |
| 6,130,316 A * | 10/2000 | Freeman et al. | |

FOREIGN PATENT DOCUMENTS

| | | |
|---|---|---|
| WO | 94/01547 | 1/1994 |
| WO | 95/03408 | 2/1995 |
| WO | WO 95/34320 | 12/1995 |
| WO | WO 96/14865 | 5/1996 |
| WO | 98/19706 | 5/1998 |

OTHER PUBLICATIONS

I. Goldberg et al. Transplant Immunology 2: 27-34 (1994).*
Azuma, M. et al., "B70 antigen is a second ligand for CTLA-2 and CD28," *Nature* 366:76-79 (1993).
Berzofsky, J.A. and Berkower, I.J., "Antigen-Antibody Interaction," In *Fundamental Immunology*, W.E. Paul eds. (NY: Raven Press), pp. 595-644 (1984).
Chen, L. et al., "Costimulation of Antitumor Immunity by the B7 Counter receptor for the T Lymphocyte Molecules CD28 and CTLA-4," *Cell* 71:1093-1102 (1992).
Co, M.S. et al., "Chimeric and Humanized Antibodies with Specificity for the CD33 Antigen," *The J. of Immunology* 148(4):1149-1154 (1992).
Cole, M.S. et al., "Human IgG2 Variants of Chimeric Anti-CD3 Are Nonmitogenic to T cells," *The J. of Immunology* 159:3613-3621 (1997).
Daikh, D. et al., "The CD28-B7 costimulatory pathway and its role in autoimmune disease," *J. of Leukocyte Biol.* 62:156-162 (1997).
Ellison, J. and Hood, J., "Linkage and sequence homology of two human immunoglobulin in γ heavy chain constant region genes," *Proc. Natl. Acad. Sci. USA* 79:1984-1988 (1982).
Engel, P. et al., "The B7-2 (B70) Costimulatory Molecule Expressed by Monocytes and Activated B Lymphocytes Is the CD86 Differentiation antigen," *Blood* 84(5):1402-1407 (1994).
Fleischer, J. et al., "Differential expression and function of CD80 (B7-1) and CD86 (B7-2) on human peripheral blood monocytes," *Immunology* 89:592-598 (1996).
Fujihara, M. et al., "Decreased Inducible Expression of CD80 and CD86 in Human Monocytes After Ultraviolet-B Irradiation: Its Involvement in Inactivation of Allogenecity," *Blood* 87(6):2386-2393 (1996).
Glaser, S.M. et al., "Dissection of the Combining Site in a Humanized Anti-Tac Antibody," *The J. of Immunology* 149(8): 2607-2614 (1992).

(Continued)

*Primary Examiner*—Phillip Gambel
(74) *Attorney, Agent, or Firm*—Finnegan Henderson Farabow Garrett & Dunner, LLP

(57) ABSTRACT

The invention relates to a humanized anti-B7-2 antibody that comprises a variable region of nonhuman origin and at least a portion of an immunoglobulin of human origin. The invention also pertains to methods of treatment for various autoimmune diseases, transplant rejection, inflammatory disorders and infectious diseases by administering humanized anti-B7-2 and/or anti-B7-1 antibodies.

18 Claims, 12 Drawing Sheets

OTHER PUBLICATIONS

He, X.-Y. et al., "Humanization and Pharmacokinetics of a Monoclonal Antibody with Specificity for Both E- and P-Selectin," *The J. of Immunology* 160:1029-1035 (1998).

Jeannin, P. et al., "CD86 (B7-2) on Human B Cells," *The J. of Biol. Chemistry* 272(25):15613-15619 (1997).

Jefferis, R. and Lund, J., "Molecular characterization of IgG antibody effector sites," *Department of Immunol.*, The Medical School, EDgbaston, Birmingham, pp. 115-126.

Levitt, M. "Molecular Dynamics of Native Protein," *J. Mol. Biol.* 168:595-620 (1983).

Morrisons, S.L. et al., "Complement activation and Fc receptor binding by IgG," In *Protein Engineering of Antibody Molecules for Prophylactic and Therapeutic Applications in Man*, M. Clark, eds. (England: Academic Titles), pp. 101-113 (1993).

Ohki, O. et al., "Functional CD86 (B7-2/B70) is predominantly expressed on Langerhans cells in atopic dermatitis," *British J. of Dermatology* 136:838-845 (1997).

Queen, C. et al., "A humanized antibody that binds to the interleukin 2 receptor," *Proc. Natl. Acad. Sci. USA* 86:1029-1033 (1989).

Reiser, H. and Schneeberger, E.E, "Expression and function of B7-1 and B7-2 in hapten-induced contact sensitivity," *Eur. J. Immunol.* 26:880-885 (1996).

Reiser, H. and Stadecker, M.J., "Costimulatory B7 Molecules in the Pathogenesis of Infection and Autoimmune Diseases," *Mechanisms of Disease* 335(18):1369-1377 (1996).

Rugtveit, J. et al., "Differential distribution of B7.1 (CD80) and B7.2 (CD86) costimulatory molecules on mucosal macrophage subsets in human inflammatory bowel disease (IBD)," *Clin. Exp. Immunol.* 110:104-113 (1997).

Shalaby, M.R. et al., "Development of Humanized Bispecific Antibodies Reactive with Cytotoxic Lymphocytes and Tumor Cells Overexpressing the HER2 Protooncogene," *J. Exp. Med.* 175:217-225 (1992).

Tempest, P.R. et al., "Reshaping A Human Monoclonal Antibody to Inhibit Human Respiratory Syncytial Virus Infection In Vivo," *Bio/Technology* 9:266-271 (1991).

Townsend, S.E. and Allison, J.P., "Tumor Rejection After Direct Costimulation of CD8+ T Cells by B7-Transfected Melanoma Cells," *Science* 259:368-369 (1993).

Yokozeki, H. et al., "Functional CD86 (B7-B70) on Cultured Human Langerhans Cells," *The Society for Investigative Dermatology, Inc.* 106:147-153 (1996).

Liu, Z-X., et al., "Increased Expression of Costimulatory Molecules on Peripheral Blood Monocytes in Patients With Crohn's Disease," *Scand. J. Gastroenterol*, 32(12):1241-6 (1997).

Lisa A. Damico, et al., "Pharmacokinetics of IV Administered Murine Anti-Human B7.1 and Murine Anti-Human B7.2 in Cynomoglus Monkeys" Abstract, 17th Annual Scientific Meeting, Jan. 9, 1998.

Cromwell, M.A. and Goldman, S.J., Abstract: "The Human PBMC-Reconstituted Nod-Scid Mouse as model of Superantigen-Induced Human T Cell Activation," Experimental Biology 98 Meeting, Apr. 22, 1998.

Bluestone, J.A., "Costimulation and its role in organ transplantation," *Clinical Transplantation* 10:104-109 (1996).

Alegre, M-L. et al., Immunomodulation of transplant rejection using monoclonal antibodies and soluble receptors, *Digestive Diseases and Sciences*, 40(1):58-64 (1995).

Bree, A.G. et al., "Humanized anti-B7-1 and anti-B7-2 antibodies prevent antigen specific induction of immunity in nonhuman primates immunized with tetanus toxoid and mumps virus vaccine," Blood, 94(10) Suppl. 1 part 1, p. 439a (1999).

Hathcock, K.S. et al., "Role of the CD28-B7 costimulatory pathways in T cell-dependent B cell responses," *Advances in Immunology*, 62:131-166 (1996).

Lenschow, D.J. et al., "Differential effects of anti-B7-1 and anti-B7-2 monoclonal antibody treatment on the development of diabetes in the nonobese diabetic mouse," *J. Exp. Med.*, 181:1145-1155 (1995).

Lenschow, D.J. et al., "Inhibition of transplant rejection following treatment with anti-B7-2 and anti-B7-1 antibodies," *Transplantation*, 60:1171-1178 (1995).

Wettendorff, M. et al., "Generation of humanized Fab fragments of B7-24 mAb, an antibody with potential use in the prevention of graft rejection and development of graft-versus-host disease," *Med. Fac. Landbouwkundige en toegepaste biologische*, 60:2057-2063 (1995).

* cited by examiner

3D1 HEAVY CHAIN VARIABLE REGION SEQUENCE

```
ATG GGT TGG AAC TGT ATC TTC ATC TTT CTG GTT ACA ACA GCT ACA GGT GTG CAC TCC CAG  60
 M   G   W   N   C   I   F   I   F   L   V   T   T   A   T   G   V   H   S   Q

GTC CAG CTG CAG CAG TCT GGG CCT GAG CTG GTG AGG CCT GGG GAA TCA GTG AAG ATT TCC  120
 V   Q   L   Q   Q   S   G   P   E   L   V   R   P   G   E   S   V   K   I   S

TGC AAG GGT TCC GGC TAC ACA TTC ACT GAT TAT GCT ATA CAG TGG GTG AAG CAG AGT CAT  180
 C   K   G   S   G   Y   T   F   T   D   Y   A   I   Q   W   V   K   Q   S   H

GCA AAG AGT CTA GAG TGG ATT GGA GTT ATT AAT ATT TAC TAT GAT AAT ACA AAC TAC AAC  240
 A   K   S   L   E   W   I   G   V   I   N   I   Y   Y   D   N   T   N   Y   N

CAG AAG TTT AAG GGC AAG GCC ACA ATG ACT GTA GAC AAA TCC TCC AGC ACA GCC TAT ATG  300
 Q   K   F   K   G   K   A   T   M   T   V   D   K   S   S   S   T   A   Y   M

GAA CTT GCC AGA TTG ACA TCT GAG GAT TCT GCC ATC TAT TAC TGT GCA AGA GCG GCC TGG  360
 E   L   A   R   L   T   S   E   D   S   A   I   Y   Y   C   A   R   A   A   W

TAT ATG GAC TAC TGG GGT CAA GGA ACC TCA GTC ACC GTC TCC TCA  390
 Y   M   D   Y   W   G   Q   G   T   S   V   T   V   S   S
```

FIG. 1(A)

3D1 LIGHT CHAIN VARIABLE REGION SEQUENCE

```
ATG GAT TCA CAG GCC CAG GTT CTT ATA TTG CTG CTA TGG GTA TCT GGT ACC TGT GGG    60
 M   D   S   Q   A   Q   V   L   I   L   L   L   W   V   S   G   T   C   G

GAC ATT GTG CTG TCA CAG TCT CCA TCC CTG GCT GTG TCA GCA GGA GAG AAG GTC ACT   120
 D   I   V   L   S   Q   S   P   S   L   A   V   S   A   G   E   K   V   T

ATG AGC TGC AAA TCC AGT CAG AGT CTG CTC AAC AGT AGA ACC CGA GAG AAC TAC TTG GCT   180
 M   S   C   K   S   S   Q   S   L   L   N   S   R   T   R   E   N   Y   L   A

TGG TAC CAG CAG AAA CCA GGG CAG TCT CCT AAA CTG CTG ATC TAC TGG GCA TCC ACT AGG   240
 W   Y   Q   Q   K   P   G   Q   S   P   K   L   L   I   Y   W   A   S   T   R

GAA TCT GGG GTC CCT GAT CGC TTC ACA GGC AGT GGA TCT GGG ACA GAT TTC ACT CTC ACC   300
 E   S   G   V   P   D   R   F   T   G   S   G   S   G   T   D   F   T   L   T

ATC AGC AGT GTG CAG GCT GAA GAC CTG GCA GTT TAT TAC TGC ACG CAA TCT TAT AAT CTT   360
 I   S   S   V   Q   A   E   D   L   A   V   Y   Y   C   T   Q   S   Y   N   L

TAC ACG TTC GGA GGG GGG ACC AAG CTG GAA ATA AAA
 Y   T   F   G   G   G   T   K   L   E   I   K
```

*FIG. 1(B)*

Hu3D1 HEAVY CHAIN VARIABLE REGION SEQUENCE

```
ATG GGT TGG AAC TGT ATC ATC TTC TTT CTG GTT ACC ACA GCT ACA GGT GTG CAC TCC CAG   60
 M   G   W   N   C   I   I   F   F   L   V   T   T   A   T   G   V   H   S   Q

GTC CAG CTG GTG CAG TCT GGG GCT GAG GTG AAG AAG CCT GGG AGC AGT CTG AAG GTG TCC  120
 V   Q   L   V   Q   S   G   A   E   V   K   K   P   G   S   S   V   K   V   S

TGC AAA GCT TCC GGC TAC ACA TTC ACT GAT TAT GCT ATA CAG TGG GTG AGA CAG GCT CCT  180
 C   K   A   S   G   Y   T   F   T   D   Y   A   I   Q   W   V   R   Q   A   P

GGA CAG GGC CTC GAG TGG ATT GGA GTT ATT AAT ATT TAC TAT GAT AAT ACA AAC TAC AAC  240
 G   Q   G   L   E   W   I   G   V   I   N   I   Y   Y   D   N   T   N   Y   N

CAG AAG TTT AAG GGC AAG GCC ACA ATG ACT GTA GAC AAG TCG ACG AGC ACA GCC TAT ATG  300
 Q   K   F   K   G   K   A   T   M   T   V   D   K   S   T   S   T   A   Y   M

GAA CTT AGT TCT TTG AGA TCT GAG GAT ACG GCC GTT TAT TAC TGT GCA AGA GCG GCC TGG  360
 E   L   S   S   L   R   S   E   D   T   A   V   Y   Y   C   A   R   A   A   W

TAT ATG GAC TAC TGG GGT CAA GGA ACC CTT GTC ACC GTC TCC TCA
 Y   M   D   Y   W   G   Q   G   T   L   V   T   V   S   S
```

FIG. 2(A)

Hu3D1 LIGHT CHAIN VARIABLE REGION SEQUENCE

```
                                                        30                                      60
ATG GAT TCA CAG GCC CAG GTT CTT ATA TTG CTG CTA TGG GTA TCT GGC ACC TGT GGG
 M   D   S   Q   A   Q   V   L   I   L   L   L   W   V   S   G   T   C   G 90                                     120
GAC ATT GTG CTG ACA CAG TCT CCA GAT TCC CTG GCT GTA TCA CTT GGA GAG AGG GCC ACT
 D   I   V   L   T   Q   S   P   D   S   L   A   V   S   L   G   E   R   A   T 150                                     180
ATT AGC TGC AAA TCC AGT CAG AGT CTG CTC AAC AGT AGA ACC CGA GAG AAC TAC TTG GCT
 I   S   C   K   S   S   Q   S   L   L   N   S   R   T   R   E   N   Y   L   A 210                                     240
TGG TAC CAG CAG AAA CCA GGG CAG CCT CCT AAA CTG CTG ATC TAC TGG GCA TCC ACT AGG
 W   Y   Q   Q   K   P   G   Q   P   P   K   L   L   I   Y   W   A   S   T   R 270                                     300
GAA TCT GGG GTC CCT GAT CGC TTC AGT GGC AGT GGA TCT GGG ACA GAT TTC ACT CTC ACC
 E   S   G   V   P   D   R   F   S   G   S   G   S   G   T   D   F   T   L   T 330                                     360
ATC AGC AGT CTG CAG GCT GAA GAC GTG GCA GTT TAT TAC TGC ACG CAA TCT TAT AAT CTT
 I   S   S   L   Q   A   E   D   V   A   V   Y   Y   C   T   Q   S   Y   N   L

390
TAC ACG TTC GGA CAG GGG ACC AAG GTG GAA ATA AAA
 Y   T   F   G   Q   G   T   K   V   E   I   K
```

METHOD OF TRANSPLANTING CELLS BY CONTACTING DONOR CELLS WITH B7-1-AND B7-2-SPECIFIC IMMUNOGLOBULINS

RELATED APPLICATION(S)

This application is a divisional of U.S. application Ser. No. 09/249,011 filed Feb. 12, 1999, the entire teachings of which are incorporated herein by reference.

BACKGROUND OF THE INVENTION

Antigen specific T-cell activation and the initiation of an immune response depend initially on the interaction of the T-cell receptor (TCR) complex with the peptide/major histocompatibility complex (MHC) present on antigen presenting cells (APC). B7 molecules, B7-1 and B7-2, are molecules which are present on APCs. A second "costimulatory" signal, provided by the interaction of B7-1 and B7-2 on the APC with their ligands CD28 and CTLA4 on T-cells, is required to complete T-cell activation and the subsequent regulation of an immune response. A need exists to regulate the B7-1 and B7-2 pathway, referred to as the B7:cD28/CTLA4 pathway. A further need exists to develop treatments for diseases that are affected by this pathway.

SUMMARY OF THE INVENTION

The invention relates to a humanized immunoglobulin having binding specificity for B7-2, wherein the immunoglobulin comprises an antigen binding region of nonhuman origin (e.g. rodent) and at least a portion of human origin (e.g. a human constant region such as an IgG constant region, a human framework region). In one embodiment, the human constant region can also contain a mutation that reduces the effector function of the humanized immunoglobulin. In another embodiment, the humanized immunoglobulin, described herein, can compete with murine 3D1 for binding to B7-2. In a particular embodiment, the antigen binding region of the humanized immunoglobulin is derived from the 3D1 monoclonal antibody.

The humanized immunoglobulin having binding specificity for B7-2 can comprise a constant region of human origin and an antigen binding region, wherein the antigen binding region of nonhuman origin comprises one or more complementarity determining regions (CDRs) of rodent origin (e.g., derived from 3D1 monoclonal antibody) that binds to B7-2, and the portion of an immunoglobulin of human origin is derived from a human framework region (FR). The antigen binding region can further comprise a light chain and a heavy chain, wherein the light and heavy chain each have three CDRs derived from the 3D1 antibody. The FR of the light chain can be derived, for example, from the light chain of the human H2F antibody and the heavy chain can be derived, for example, from the heavy chain of the human I2R antibody. In a particular embodiment, the invention is a humanized immunoglobulin having binding specificity for B7-2 that is derived from the cell line deposited with the American Type Culture Collection (A.T.C.C.), Accession No. CRL-12524.

The invention also embodies a humanized immunoglobulin having a binding specificity for B7-2 comprising a heavy chain and/or a light chain. The light chain comprises a CDR (e.g., CDR1, CDR2 and CDR3) derived from an antibody of nonhuman origin which binds B7-2 and a FR derived from a light chain of human origin (e.g., H2F antibody). The heavy chain comprises a CDR (e.g.,CDR1, CDR2 and CDR3) derived from an antibody of nonhuman origin which binds B7-2 and a FR region derived from a heavy chain of human origin (e.g., the human III2R antibody). The immunoglobulin can further comprise CDR1, CDR2 and CDR3 for the light or heavy chain having the amino acid sequence set forth herein or an amino acid.

One embodiment of the invention is a humanized-immunoglobulin light chain having binding specificity for B7-2 comprising CDR1, CDR2 and/or CDR3 of the light chain of murine 3D1 antibody, and a human light chain FR (e.g., H2F antibody). Another embodiment is a humanized immunoglobulin light chain that comprises a variable region shown in FIG. 2B (SEQ ID NO: 8). The invention also relates to an isolated nucleic acid sequence that encodes a humanized variable light chain specific for B7-2 that comprises a nucleic acid, such as the sequence shown in FIG. 2B (SEQ ID NO: 7), a nucleic acid that encodes the amino acid sequence shown in FIG. 2B (SEQ ID NO: 8), a nucleic acid which hybridizes thereto under stringent hybridization conditions, and a nucleic acid which is the complement thereof.

Another embodiment of the invention is a humanized immunoglobulin heavy chain that is specific for B7-2 and comprises CDR1, CDR2 and/or CDR3 of the heavy chain of the 3D1 antibody, and a human heavy chain FR (e.g., III2R antibody). The invention pertains to a humanized immunoglobulin heavy chain that comprises a variable region shown in FIG. 2A (SEQ ID NO: 6). The invention also pertains to an isolated nucleic acid sequence that encodes a humanized variable heavy chain specific for B7-2 that comprises a nucleic acid, such as the sequence shown in FIG. 2A (SEQ ID NO: 5), a nucleic acid that encodes the amino acid sequence shown in FIG. 2A (SEQ ID NO: 6), a nucleic acid which hybridizes thereto under stringent hybridization conditions, and a nucleic acid which is the complement thereof.

In particular, an embodiment of the invention is a humanized immunoglobulin which specifically binds to B7-2 and comprises a humanized light chain comprising three light chain CDRs from the mouse 3D 1 antibody and a light chain variable region framework sequence from a human immunoglobulin light chain, and a humanized heavy chain comprising three heavy chain CDRs from the mouse 3D 1 antibody and a heavy chain variable region framework sequence from a human immunoglobulin heavy chain. The mouse 3D1 antibody can further have a mature light chain variable domain, such as the mature light chain variable domain shown in FIG. 1B (SEQ ID NO.: 4) and a mature heavy chain variable domain such as the mature heavy chain variable region shown in FIG. 1A (SEQ ID NO.: 2).

The invention includes an expression vector that comprises a fused gene which encodes a humanized immunoglobulin light and/or heavy chain. The gene comprises a nucleotide sequence encoding a CDR derived from a light and/or heavy chain of a nonhuman antibody having binding specificity for B7-2 (e.g., murine 3D1 antibody) and a FR derived from a light and/or heavy chain of human origin.

The present invention also relates to a host cell comprising a nucleic acid of the present invention, including one or more constructs comprising nucleic acid of the present invention. In one embodiment, the invention encompasses a host cell comprising a first recombinant nucleic acid that encodes a humanized immunoglobulin light chain and a second recombinant nucleic acid that encodes a humanized immunoglobulin heavy chain. The first nucleic acid comprises a nucleotide sequence encoding a CDR derived from the light chain of murine 3D1 antibody and a FR derived from a light chain of human origin. The second nucleic acid comprises a nucleotide sequence encoding a CDR derived from the heavy chain of murine 3D 1 antibody and a FR derived from a heavy chain of human origin. The invention further relates to a host cell comprising a vector or a nucleic acid that encodes the humanized immunoglobulin, as described herein.

The invention further pertains to methods of preparing a humanized immunoglobulin that comprise maintaining a host cell that encodes a humanized immunoglobulin that is specific for B7-2, as described herein, under conditions appropriate for expression of a humanized immunoglobulin, wherein a humanized immunoglobulin chain (one or more) are expressed and a humanized immunoglobulin is produced. The method further comprises the step of isolating the humanized immunoglobulin.

Additional methods encompassed by the invention include a method of inhibiting the interaction of a first cell bearing a B7-2 receptor with a second cell bearing B7-2, comprising contacting the second cell with an effective amount of a humanized immunoglobulin, as described herein. Accordingly, the invention relates to various methods of treatment. The invention includes a method for modulating an immune response of a patient or treating a patient having a transplanted organ, tissue, cell or the like comprising administering an effective amount of the humanized immunoglobulin, as described herein, in a carrier (e.g., pharmaceutical carrier), wherein the immune response is modulated. The invention pertains to treating acute and/or chronic transplant rejection for a prolonged periods of time (e.g., days, months, years). The invention also pertain to methods of treating a disease associated with modulation of the B7-2 molecule (e.g., autoimmune diseases, infectious diseases, inflammatory disorders, systemic lupus erythematosus, diabetes mellitus, insulitis, arthritis, inflammatory bowel disease, inflammatory dermatitis, and multiple sclerosis), comprising administering to a patient an effective amount (e.g., a therapeutically effective amount) of a humanized immunoglobulin, as described herein, in a carrier. Accordingly, the invention encompasses a pharmaceutical composition comprising the humanized antibody, as described herein.

The invention also embodies a method of making a humanized immunoglobulin specific to B7-2 from a murine antibody specific to B7-2. The method comprises determining the CDRs of an antibody of non-human origin (e.g., murine origin) which has binding specificity for B7-2; obtaining a human antibody having a framework region amino acid sequence suitable for grafting of the CDRs, and grafting the CDRs of an antibody of non-human origin into the FR of the human antibody.

The invention also relates to a method for determining the presence or absence of B7-2 in a sample. The method comprises obtaining the sample to be tested, contacting the sample with a humanized antibody specific to B7-2, or a fragment thereof, sufficiently to allow formation of a complex between B7-2 and the anti-B7-2 antibody, and detecting the presence or absence of the complex formation. The presence of the complex indicates the presence of B7-2 in the sample.

The invention relates to methods for treating a patient having a disease comprising administering a therapeutically effective amount of a humanized immunoglobulin specific to B7-1 and a therapeutically effective amount of a humanized immunoglobulin specific to B7-2. The diseases, as described herein, include, for example, autoimmune diseases, infectious diseases, asthma, inflammatory disorders, systemic lupus erythematosus, diabetes mellitus, insulitis, arthritis, inflammatory bowel disease, inflammatory dermatitis, and multiple sclerosis. This method also pertains to modulating the immune response of a patient having a transplanted organ, tissue, cell or the like comprising administering an effective amount of a humanized immunoglobulin that binds to B7-1 and a humanized immunoglobulin that binds to B7-2. Such diseases are described herein.

The invention also pertains to methods for transplanting cells (e.g., bone marrow, or blood cells or components) to a patient in need thereof comprising obtaining cells (e.g., bone marrow, or blood cells or components) from a donor, contacting the cells with an immunoglobulin specific to B7-1, an immunoglobulin specific to B7-2 and recipient cells, thereby obtaining a mixture. The immunoglobulins and the recipient cells are maintained for a period of time sufficient for tolerance induction. The mixture (e.g., bone marrow or blood cell composition) is then introduced into the patient. The recipient cells comprise a lymphocyte antigen (e.g. lymphocytes that express class 1 antigens (MHCI) or peripheral blood lymphocyte (PBL)). Instead of using recipient cells, the method also comprise utilizing tissue, organs or cells that express MHC Class I antigens, B7-1 and/or B7-2 molecules. The cells can be engineered to express recipient molecules. The cells from the donor can be bone marrow cells or cells/components from blood (e.g., stem cells or immature cells). The B7 immunoglobulins are in contact with the donor bone marrow and the recipient cells for a period of time that is long enough to induce tolerance induction (e.g., about 1 to 48 hours, and, preferably about 36 hours). A patient in need of such a transplant is one who has a disease that is benefitted by or treatable with a bone marrow transplant. Such diseases, for example, are proliferative diseases (e.g. leukemia, lymphoma and cancer), anemia (e.g. sickle-cell anemia, thalassemia, and aplastic anemia) and myeloid dysplasia syndrome (MDS).

The invention includes methods for transplanting bone marrow to a patient having a disease (e.g., proliferative diseases such as leukemia, lymphoma, cancer; anemia (e.g., sickle-cell anemia, thalassemia, and aplastic anemia) and myeloid dysplasia syndrome that is treated with a bone marrow transplant comprising obtaining bone marrow from a donor, and contacting the bone marrow with an immunoglobulin specific to B7-1 and/or an immunoglobulin specific to B7-2 and recipient cells (e.g., lymphocyte). The bone marrow, immunoglobulin(s) and recipient cells are in contact for a period of time sufficient for tolerance induction (e.g., about 1–48 hours, preferably about 36 hours). The method then comprises re-introducing the treated bone marrow to the patient.

Advantages of the invention include the ability to regulate or modulate the B7 costimulatory pathway. Manipulation of this costimulatory pathway with a humanized anti-B7-2 and/or anti-B7-1 antibody provides methods of treatments for various diseases. The humanized B7-2 antibody maintains about the same specificity for B7-2 as the murine 3D1 antibody, but with a reduced immunogenicity in humans. Accordingly, the invention can advantageously be used to treat immune-related diseases/disorders or diseases in which the B7-2 molecule plays an important role. Particularly, the invention relates to methods for treating infectious or autoimmune diseases and methods for modulating the immune response for patients with transplanted organs, tissue or cells.

BRIEF DESCRIPTION OF THE FIGURES

The foregoing and other embodiments, features and advantages of the invention will be apparent from the following more particular description of preferred embodiments of the invention, as illustrated in the accompanying figures.

FIG. 1A is a sequence listing illustrating the heavy chain variable region nucleic acid and amino acid sequences (SEQ ID NOS: 1 and 2, respectively) of the murine 3D1 antibody, wherein the amino acid sequences of the CDRs (CDR1, CDR2 and CDR3) are underlined and the first amino acids of the mature chains are double underlined.

FIG. 1B is a sequence listing illustrating the light chain variable region nucleic acid and amino acid sequences (SEQ ID NOS: 3 and 4, respectively) of the murine 3D1 antibody wherein, the nucleic and amino acid sequences of the CDRs (CDR1, CDR2 and CDR3) are underlined and the first amino acids of the mature chains are double underlined.

FIG. 2A is a sequence listing illustrating the heavy chain variable region nucleic acid and amino acid sequences (SEQ ID NOs: 5 and 6, respectively) of the humanized 3D 1 antibody, wherein the nucleic and amino acid sequences of the CDRs (CDR1, CDR2 and CDR3) are underlined and the first amino acids of the mature chains are double underlined.

FIG. 2B contains the light chain variable region nucleic acid and amino acid sequences (SEQ ID NOs: 7 and 8, respectively) of the humanized 3D1 antibody, wherein the nucleic and amino acid sequences of CDR1, CDR2 and CDR3. The CDRs are underlined and the first amino acids of the mature chains are double underlined.

DETAILED DESCRIPTION OF THE INVENTION

Figure 3:
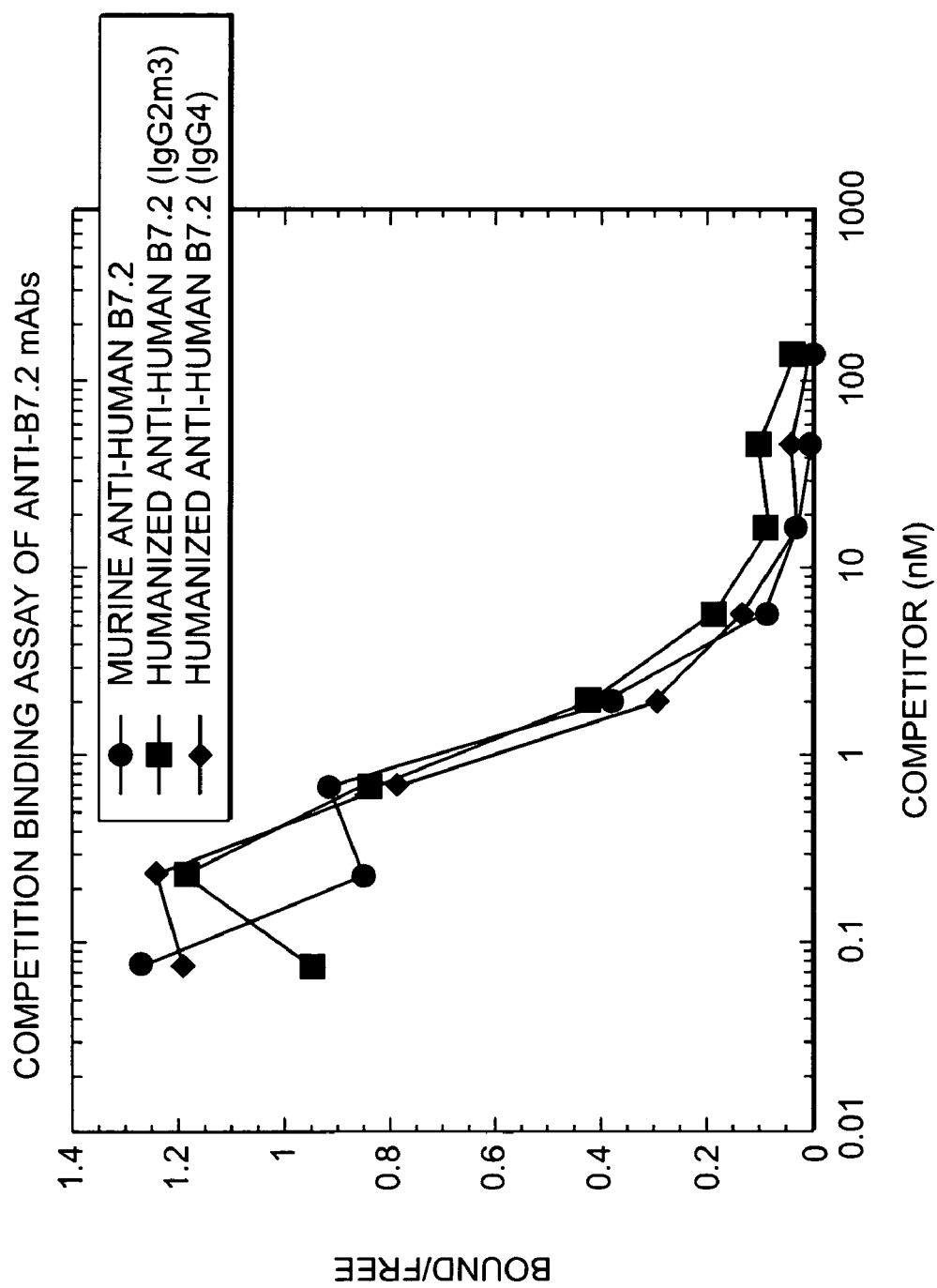
FIG. 3 is a graph of competitive binding assays. The graph depicts the results of a competitive binding assay of murine or humanized anti-human B7-2 mAbs to CHO expressing rhB7-2 (CHO/hB7-2) on their surface. Increasing concentrations of unlabelled competitor antibodies were incubated with CHO/hB7-2 cells in the presence of radiolabelled tracer murine anti-human B7-2 mAb and the ratio of bound/free antibody was determined.

The invention relates to a humanized immunoglobulin having binding specificity for B7-2, comprising an antigen binding region of nonhuman origin and at least a portion of an immunoglobulin of human origin. Preferably, the humanized immunoglobulins can bind B7-2 with an affinity of at least about $10^7 M^{-1}$, preferably at least about $10^8 M^{-1}$, and more preferably at least about $10^9 M^{-1}$. In one embodiment, the humanized immunoglobulin includes an antigen binding region of nonhuman origin which binds B7-2 and a constant region derived from a human constant region. The human constant region can have non-human residues in the framework region. In another embodiment, the humanized immunoglobulin which binds B7-2 comprises a complementarity determining region (one or more) of nonhuman origin and a variable framework region (one or more) of human origin, and optionally, a constant region of human origin. Optionally, the FR region of the immunoglobulin can comprise residues of non-human origin. For example, the humanized immunoglobulin can comprise a heavy chain and a light chain, wherein the light chain comprises a complementarity determining region derived from an antibody of nonhuman origin which binds B7-2 and a framework region derived from a light chain of human origin, and the heavy chain comprises a complementarity determining region derived from an antibody of nonhuman origin which binds B7-2 and a framework region derived from a heavy chain of human origin. Also, the invention, individually or in a functional combination, embodies the light chain, the heavy chain, the variable region, the variable light chain and the variable heavy chain.

The invention relates to a humanized B7-2 antibody that possesses substantially the same binding specificity as the murine B7-2 antibody (e.g., 3D1) from which the humanized antibody is made, but with reduced immunogenicity in primates (e.g., humans). The humanized B7-2 antibody has about a lessor, substantially the same, or greater binding affinity as the murine counterpart. See FIGS. 3 and 4.

Naturally occurring immunoglobulins have a common core structure in which two identical light chains (about 24 kD) and two identical heavy chains (about 55 or 70 kD) form a tetramer. The amino-terminal portion of each chain is known as the variable (V) region, also referred to as the "antigen binding" region, and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. The variable region is the portion of the antibody that binds to the antigen. The constant region allows for various functions such as the ability to bind to Fc receptors on phagocytic cells, placental cells, mast cells, etc. The light and heavy chains each have a variable region and a constant region. Accordingly, the invention relates to a humanized immunoglobulin having binding specificity to B7-2. The humanized immunoglobulin comprises a light chain and a heavy chain in which two light chains and two heavy chains form the tetramer.

The variable region further constitutes two types of regions, a framework region (FR) and a complementarity determining region (CDR). CDRs are hypervariable regions that contain most of the amino acid sequence variation in between immunoglobulins. Proceeding from the amino-terminus, these regions are designated CDR1, CDR2 and CDR3, respectively. See FIGS. 1A–1B and 2A–2B. The CDRs are connected by more conserved FRs. Proceeding from the amino-terminus, these regions are designated FR1, FR2, FR3, and FR4, respectively. The locations of CDR and FR regions and a numbering system have been defined by Kabat et al. (Kabat, E. A. et al., *Sequences of Proteins of Immunological Interest*, Fifth Edition, U.S. Department of Health and Human Services, U.S. Government Printing Office (1991); Kabat, E. A. *Structural Concepts in Immunology and Immunochemistry*, Second Edition, Holt, Rinehart and Winston, N.Y. (1976); Kabat, E. A. *Sequences of Immunoglobulin Chains: Tabulation and Analysis of Amino Acid Sequences of Precurrsors, V-regions, C-regions, J-Chain and β2-Microglobulins*, U.S. Department of Health, Education and Welfare, Public Health Service, (1979); Kabat, E. A. *Structural Concepts in Immunology and Immunochemistry*, Holt, Rinehart and Winston, N.Y. (1968); Kabat, E. A. *Experimental Immunochemistry*, Second Edition, Springfield, Thomas (1967). During the process of humanizing an immunoglobulin, one or more of the CDRs from an antibody having specificity for B7-2 from a non-human species is grafted into the FRs of a human antibody. In addition, certain non-human framework substitutes can be made according to the methods described herein. The resulting humanized antibody has CDRs from a non-human species such as a mouse and FRs from a human antibody, whereby the humanized antibody maintains its antigenic specificity and affinity to B7-2.

The invention also relates to a humanized immunoglobulin light chain or a humanized immunoglobulin heavy chain. In one embodiment, the invention relates to a humanized light chain comprising one or more light chain CDRs (e.g., CDR1 (SEQ ID NO: 16), CDR2 (SEQ ID NO: 18) and/or CDR3 (SEQ ID NO: 20)) of nonhuman origin and a human light chain framework region (See FIG. 2B). In another embodiment, the invention relates to a humanized immunoglobulin heavy chain comprising one or more heavy chain CDRs (e.g., CDR1 (SEQ ID NO: 10), CDR2 (SEQ ID NO: 12), and/or CDR3 (SEQ ID NO: 14)) of nonhuman origin and a human heavy chain framework region (See FIG. 2A). The CDRs can be derived from a nonhuman immunoglobulin such as murine heavy (e.g., SEQ ID NO: 1, FIG. 1A) and light (e.g., SEQ ID NO: 3, FIG. 1B) variable region chains which are specific to B7-2.

The invention also embodies the humanized anti-B7-2 antibody expressed by a cell line deposited with the A.T.C.C., 10801 University Boulevard, Manassas, Va. 02110-2209, on May 5, 1998, A.T.C.C. No: CRL-12524. The cell line which expresses the humanized anti-B7-2 antibody, deposited with the A.T.C.C., is designated as a recombinant CHO cell line (PA-CHO-DUKX-1538) expressing the humanized anti-human B7-2 (CD86) monoclonal antibody (#HF2-3D1) of the IgG2.M3 isotype.

Human immunoglobulins can be divided into classes and subclasses, depending on the isotype of the heavy chain. The classes include IgG, IgM, IgA, IgD and IgE, in which the heavy chains are of the gamma (γ), mu (μ), alpha (αc), delta (δ) or epsilon (ε) type, respectively. Subclasses include IgG1, IgG2, IgG3, IgG4, IgA1 and IgA2, in which the heavy chains are of the γ1, γ2, γ3, γ4, α1 and α2 type, respectively. Human immunoglobulin molecules of a selected class or subclass may contain either a kappa (κ) or lambda (λ) light chain. See e.g., *Cellular and Molecular Immunology*, Wonsiewicz, M. J., Ed., Chapter 45, pp. 41–50, W.B. Saunders Co, Philadelphia, Pa. (1991); Nisonoff, A., *Introduction to Molecular Immunology*, 2nd Ed., Chapter 4, pp. 45–65, Sinauer Associates, Inc., Sunderland, Mass. (1984).

The terms "HF2.3D1" and "3D1" refer to a murine immunoglobulin specific to B7-2. The terms "humanized HF2.3D1," "humanized 3D1" and "hu3D1" refer to a humanized immunoglobulin specific to B7-2.

The terms "immunoglobulin" or "antibody" include whole antibodies and biologically functional fragments thereof. Such biologically functional fragments retain at least one antigen binding function of a corresponding full-length antibody (e.g., for B7-2) and preferably, retain the ability to inhibit the interaction of B7-2 with one or more of its receptors (e.g., CD28, CTLA-4). In a preferred embodiment, biologically functional fragments can inhibit binding of B7-2 for manipulation of the co-stimulatory pathway. Examples of biologically functional antibody fragments which can be used include fragments capable of binding to an B7-2, such as single chain antibodies, Fv, Fab, Fab' and F(ab')$_2$ fragments. Such fragments can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a chimeric gene encoding the heavy chain of an F(ab')$_2$ fragment can be designed to include DNA sequences encoding the CH domain and hinge region of the heavy chain. The invention includes single chain antibodies (e.g., a single chain FV) that contain both portions of the heavy and light chains.

The term "humanized immunoglobulin" as used herein refers to an immunoglobulin comprising portions of immunoglobulins of different origin, wherein at least one portion is of human origin. For example, the humanized antibody can comprise portions derived from an immunoglobulin of nonhuman origin with the requisite specificity, such as a mouse, and from immunoglobulin sequences of human origin (e.g., chimeric immunoglobulin). These portions can be joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin of the invention is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., *Science,* 242: 423–426 (1988)), regarding single chain antibodies.

As embodied in the exemplified antibody of the present invention, the term "humanized immunoglobulin" also refers to an immunoglobulin comprising a human framework, at least one CDR from a non-human antibody, and in which any constant region present is substantially identical to a human immunoglobulin constant region, e.g., at least about 60–90%, preferably at least 95% identical. Hence, all parts of a humanized immunoglobulin, except possibly the CDR's, are substantially identical to corresponding parts of one or more native human immunoglobulin sequences. In some instances, the humanized immunoglobulin, in addition to CDRs from a non-human antibody, would include additional non-human residues in the human framework region.

The design of humanized immunoglobulins can be carried out as follows. When an amino acid falls under the following categories, the framework amino acid of a human immunoglobulin to be used (acceptor immunoglobulin) is replaced by a framework amino acid from a CDR-providing non-human immunoglobulin (donor immunoglobulin):

(a) the amino acid in the human framework region of the acceptor immunoglobulin is unusual for human immunoglobulin at that position, whereas the corresponding amino acid in the donor immunoglobulin is typical for human immunoglobulin in that position:

(b) the position of the amino acid is immediately adjacent to one of the CDR's; or (c) the amino acid is capable of interacting with the CDR's in a tertiary structure immunoglobulin model (see, Queen et al., op. cit., and Co et al., Proc. Natl. Acad. Sci. USA 88, 2869 (1991)).

For a detailed description of the production of humanized immunoglobulins, See Queen et al., op. cit. and Co et al, op. cit. and U.S. Pat. Nos. 5,585,089; 5,693,762, 5,693,761, and 5,530,101.

Usually, the CDR regions in humanized antibodies are substantially identical, and more usually, identical to the corresponding CDR regions in the mouse antibody from which they were derived. Although not usually desirable, it is sometimes possible to make one or more conservative amino acid substitutions of CDR residues without appreciably affecting the binding affinity of the resulting humanized immunoglobulin. Occasionally, substitutions of CDR regions can enhance binding affinity.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin.

The antigen binding region of the humanized immunoglobulin (the non-human portion) can be derived from an immunoglobulin of nonhuman origin, referred to as a donor immunoglobulin, having specificity for B7-2. For example, a suitable antigen binding region can be derived from the murine HF2.3D1 monoclonal antibody. U.S. Ser. No. 08/101,624, filed on Jul. 26, 1993, Ser. No. 08/109,393, filed Aug. 19, 1993 and 08/147,773, filed Nov. 3, 1993, entitled, "B7-2:CTLA4/CD28 Counter Receptor". See also, Freeman, et al., WO 95/03408, "B7-2: CTLA4/CD 28 Counter Receptor, published on Feb. 2, 1995. Other sources include B7-2-specific antibodies obtained from nonhuman sources, such as rodent (e.g., mouse and rat), rabbit, pig, goat or non-human primate (e.g., monkey) or camelid animals (e.g., camels and llamas).

Additionally, other polyclonal or monoclonal antibodies, such as antibodies which bind to the same or similar epitope as the murine HF2.3D1 antibody, can be made (e.g., Kohler et al., *Nature,* 256:495–497 (1975); Harlow et al., 1988, Antibodies: A Laboratory Manual, (Cold Spring Harbor, N.Y.); and Current Protocols in Molecular Biology, Vol. 2 (Supplement 27, Summer '94), Ausubel et al., Eds. (John Wiley & Sons: New York, N.Y.), Chapter 11(1991)). For example, antibodies can be raised against an appropriate immunogen in a suitable mammal such as a mouse, rat, rabbit, sheep, or camelid. Cells bearing B7-2, membrane fractions containing B7-2, immunogenic fragments of B7-2, and a B7-2 peptide conjugated to a suitable carrier are examples of suitable immunogens (e.g., DNA or peptide immunogens). Antibody-producing cells (e.g., a lymphocyte) can be isolated, for example, from the lymph nodes or spleen of an immunized animal. The cells can then be fused to a suitable immortalized cell (e.g., a myeloma cell line), thereby forming a hybridoma. Fused cells can be isolated employing selective culturing techniques. Cells which produce antibodies with the desired specificity can be selected by a suitable assay, such as an ELISA. Immunoglobulins of nonhuman origin having binding specificity for B7-2 can also be obtained from antibody libraries, such as a phage library comprising nonhuman Fab molecules. Humanized immunoglobulins can be made using molecular biology techniques, Abgenics, or CAT techniques.

In one embodiment, the antigen binding region of the humanized immunoglobulin comprises a CDR of nonhuman origin. In this embodiment, the humanized immunoglobulin having binding specificity for B7-2 comprises at least one CDR of nonhuman origin. For example, CDRs can be derived from the light and heavy chain variable regions of immunoglobulins of nonhuman origin, such that a humanized immunoglobulin includes substantially the heavy chain CDR1 (e.g., SEQ ID NO: 10), CDR2 (e.g., SEQ ID NO: 12) and/or CDR3 (e.g., SEQ ID NO: 14) amino acid sequences, and/or light chain CDR1 (e.g., SEQ ID NO: 16), CDR2 (e.g., SEQ ID NO: 18) and/or CDR3 (e.g., SEQ ID NO: 20) amino acid sequences, from one or more immunoglobulins of nonhuman origin, and the resulting humanized immunoglobulin has binding specificity for B7-2. All three CDRs of a selected chain can be substantially the same as the CDRs of the corresponding chain of a donor, and preferably, all three CDRs of the light and heavy chains are substantially the same as the CDRs of the corresponding donor chain. The nucleic acid sequences of the heavy chain CDR1 (e.g., SEQ ID NO: 9), CDR2 (e.g., SEQ ID NO: 11) and CDR3 (e.g., SEQ ID NO: 13) and/or light chain CDR1 (e.g., SEQ ID NO: 15), CDR2 (e.g., SEQ ID NO: 17), and CDR3 (e.g., SEQ ID NO: 19) can also be used in grafting the CDRs into the human framework.

In another embodiment, the invention pertains to a humanized immunoglobulin having a binding specificity for B7-2 comprising a heavy chain and a light chain. The light chain can comprise a CDR derived from an antibody of nonhuman origin which binds B7-2 and a FR derived from a light chain of human origin. For example, the light chain can comprise CDR1, CDR2 and/or CDR3 which have the amino acid sequence set forth below or an amino acid substantially the same as the amino acid sequence such that the antibody specifically binds to the B7-2: CDR1 KSSQSLLNSRTRENYLA (SEQ ID NO: 16), CDR2 WASTRES (SEQ ID NO: 18), and CDR3 TQSYNLYT (SEQ ID NO: 20). The heavy chain can comprise a CDR derived from an antibody of nonhuman origin which binds B7-2 and a FR derived from a heavy chain of human origin. For example, the heavy chain can comprise CDR1, CDR2 and CDR3 which have the amino acid sequence set forth below or an amino acid substantially the same as said amino acid sequence such that the antibody specifically binds to the B7-2: heavy chain: CDR1 DYAIQ (SEQ ID NO: 10), CDR2 VINIYYDNTNYNQKFKG (SEQ ID NO: 12), CDR3 AAWYMDY (SEQ ID NO: 14).

An embodiment of the invention is a humanized immunoglobulin which specifically binds to B7-2 and comprises a humanized light chain comprising three light chain CDRs from the mouse 3D1 antibody and a light chain variable region framework sequence from a human immunoglobulin light chain. The invention further comprises a humanized heavy chain that comprises three heavy chain CDRs from the mouse 3D1 antibody and a heavy chain variable region framework sequence from a human immunoglobulin heavy chain. The mouse 3D1 antibody can further have a mature light chain variable domain as shown in FIG. 1B (SEQ ID NO.: 4) and a mature heavy chain variable domain as shown in FIG. 1A (SEQ ID NO.: 2).

The portion of the humanized immunoglobulin or immunoglobulin chain which is of human origin (the human portion) can be derived from any suitable human immunoglobulin or immunoglobulin chain. For example, a human constant region or portion thereof, if present, can be derived from the κ or λ light chains, and/or the γ (e.g., γ1, γ2, γ3, γ4), μ, α (e.g., α1, α2), δ or ε heavy chains of human antibodies, including allelic variants. A particular constant region, such as IgG2 or IgG4, variants or portions thereof can be selected to tailor effector function. For example, a mutated constant region, also referred to as a "variant," can be incorporated into a fusion protein to minimize binding to Fc receptors and/or ability to fix complement (see e.g., Winter et al., U.S. Pat. Nos. 5,648,260 and 5,624,821; GB 2,209,757 B; Morrison et al., WO 89/07142; Morgan et al., WO 94/29351, Dec. 22, 1994). In addition, a mutated IgG2 Fc domain can be created that reduces the mitogenic response, as compared to natural FC regions (see e.g., Tso et al., U.S. Pat. No. 5,834,597, the teachings of which are incorporated by reference herein in their entirety). See Example 3 for mutations performed to the humanized anti-B7-2 antibody.

If present, human FRs are preferably derived from a human antibody variable region having sequence similarity to the analogous or equivalent region of the antigen binding region donor. Other sources of FRs for portions of human origin of a humanized immunoglobulin include human variable consensus sequences (See, Kettleborough, C. A. et al., *Protein Engineering* 4:773–783 (1991); Queen et al., U.S. Pat. Nos. 5,585,089, 5,693,762 and 5,693,761, the teachings all of which are incorporated by reference herein in their entirety). For example, the sequence of the antibody or variable region used to obtain the nonhuman portion can be compared to human sequences as described in Kabat, E. A., et al., *Sequences of Proteins of Immunological Interest*, Fifth Edition, U.S. Department of Health and Human Services, U.S. Government Printing Office (1991). In a preferred embodiment, the FRs of a humanized immunoglobulin chain are derived from a human variable region having at least about 60% overall sequence identity, and preferably at least about 80% overall sequence identity, with the variable region of the nonhuman donor (e.g., murine HF2.3D1 antibody). For example, the overall sequence identity between the mouse HF2.3D1 and human H2F light chain variable framework regions is 82.5%, and the overall sequence identity between the mouse HF2.3D1 and human I2R heavy chain variable framework regions is 62.5%.

The phrase "substantially identical," in context of two nucleic acids or polypeptides (e.g., DNAs encoding a humanized immunoglobulin or the amino acid sequence of the humanized immunoglobulin) refers to two or more sequences or subsequences that have at least about 80%, most preferably 90–95% or higher nucleotide or amino acid residue identity, when compared and aligned for maximum correspondence, as measured using the following sequence comparison method and/or by visual inspection. Such "substantially identical" sequences are typically considered to be homologous. Preferably, the "substantial identity" exists over a region of the sequences that is at least about 50 residues in length, more preferably over a region of at least about 100 residues, and most preferably the sequences are substantially identical over at least about 150 residues, or over the full length of the two sequences to be compared. As described below, any two antibody sequences can only be aligned in one way, by using the numbering scheme in Kabat. Therefore, for antibodies, percent identity has a unique and well-defined meaning.

Amino acids from the variable regions of the mature heavy and light chains of immunoglobulins are designated Hx and Lx respectively, where x is a number designating the position of an amino acid according to the scheme of Kabat, *Sequences of Proteins of Immunological Interest* (National Institutes of Health, Bethesda, Md., 1987 and 1991). Kabat lists many amino acid sequences for antibodies for each subgroup, and lists the most commonly occurring amino acid for each residue position in that subgroup. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat. The use of the Kabat numbering system readily identifies amino acids at equivalent positions in different antibodies. For example, an amino acid at the L50 position of a human antibody occupies the equivalent position to an amino acid position L50 of a mouse antibody.

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function. The variable regions of each light/ heavy chain pair form the antibody binding site. Thus, an intact antibody has two binding sites.

Light chains are classified as either kappa or lambda. Heavy chains are classified as gamma, mu, alpha, delta, or epsilon, and define the antibody's isotype as IgG, IgM, IgA, IgD, and IgE, respectively. Within light and heavy chains, the variable and constant regions are joined by a "J" region of about 12 or more amino acids, with the heavy chain also including a "D" region of about 10 more amino acids. See generally, *Fundamental Immunology*, Paul, W., ed., 3rd ed. Raven Press, N.Y., 1993, Ch. 9).

From N-terminal to C-terminal, both light and heavy chain variable regions comprise alternating framework and (CDRs)" FR1, CDR1, FR2, CDR2, FR3, CDR3 and FR4. The assignment of amino acids to each region is in accordance with the definitions of Kabat (1987) and (1991), supra and/or Chothia & Lesk, *J. Mol. Biol.* 196:901–917 (1987); Chothia et al., *Nature* 342:878–883 (1989).

In one embodiment, the humanized immunoglobulin comprises at least one of the FRs derived from one or more chains of an antibody of human origin. Thus, the FR can include a FR1, FR2, FR3 and/or FR4 derived from one or more antibodies of human origin. Preferably, the human portion of a selected humanized chain includes FR1, FR2, FR3 and/or FR4 derived from a variable region of human origin (e.g., from a human immunoglobulin chain, from a human consensus sequence). In a preferred embodiment, the FRs for the light chain variable region are from the H2F human antibody and the FRs for the heavy chain variable region are from the I2R human antibody.

The immunoglobulin portions of nonhuman and human origin for use in the invention have sequences that are identical to immunoglobulins or immunoglobulin portions from which they are derived, or to variants thereof. Such variants include mutants differing by the addition, deletion, or substitution of one or more residues. As indicated above, the CDRs which are of nonhuman origin are substantially the same as in the nonhuman donor, and preferably are identical to the CDRs of the nonhuman donor. As described herein, changes in the FR, such as those which substitute a residue of the FR of human origin with a residue from the corresponding position of the donor can be made. One or more mutations in the FR can be made, including deletions, insertions and substitutions of one or more amino acids. Several such substitutions are described in the design of a humanized HF2.3D1 antibody in Example 2. For a selected humanized antibody or chain, framework mutations can be designed as described herein. Preferably, the humanized immunoglobulins can bind B7-2 with an affinity similar to or better than that of the nonhuman donor. Variants can be produced by a variety of suitable methods, including mutagenesis of nonhuman donor or acceptor human chains.

The humanized immunoglobulins of the invention have binding specificity for human B7-2, and include humanized immunoglobulins (including fragments) which can bind determinants of B7-2. In a preferred embodiment, the humanized immunoglobulin of the present invention has at least one functional characteristic of murine HF2.3D1 antibody, such as binding function (e.g., having specificity for B7-2, having the same or similar epitopic specificity), and/or inhibitory function (e.g., the ability to inhibit the binding of a cell bearing CD28 or CTLA-4 to the B7-2 ligand). Thus, preferred humanized immunoglobulins can have the binding specificity of the murine HF2.3D 1 antibody, the epitopic specificity of the murine HF2.3D1 antibody (e.g., can compete with murine HF2.3D1, a chimeric HF2.3D1 antibody, or humanized HF2.3D1 for binding to B7-2) and/or inhibitory function.

The binding function of a humanized immunoglobulin having binding specificity for B7-2 can be detected by standard immunological methods, for example using assays which monitor formation of a complex between humanized immunoglobulin and B7-2 (e.g., a membrane fraction comprising B7-2, or human lymphocyte cell line or recombinant host cell comprising nucleic acid which expresses B7-2).

Binding and/or adhesion assays or other suitable methods can also be used in procedures for the identification and/or isolation of humanized immunoglobulins (e.g., from a library) with the requisite specificity (e.g., an assay which monitors adhesion between a cell bearing a B7-2 receptor and B7-2, or other suitable methods).

The immunoglobulin portions of nonhuman and human origin for use in the invention include light chains, heavy chains and portions of light and heavy chains. These immunoglobulin portions can be obtained or derived from immunoglobulins (e.g., by de novo synthesis of a portion), or nucleic acids encoding an immunoglobulin or chain thereof having the desired property (e.g., binds B7-2, sequence similarity) can be produced and expressed. Humanized immunoglobulins comprising the desired portions (e.g., antigen binding region, CDR, FR, C region) of human and nonhuman origin can be produced using synthetic and/or recombinant nucleic acids to prepare genes (e.g., cDNA) encoding the desired humanized chain. To prepare a portion of a chain, one or more stop codons can be introduced at the desired position. For example, nucleic acid sequences coding for newly designed humanized variable regions can be constructed using PCR mutagenesis methods to alter existing DNA sequences (see e.g., Kamman, M., et al., *Nucl. Acids Res.* 17:5404 (1989)). PCR primers coding for the new CDRs can be hybridized to a DNA template of a previously humanized variable region which is based on the same, or a very similar, human variable region (Sato, K., et al., *Cancer Research* 53:851–856 (1993)). If a similar DNA sequence is not available for use as a template, a nucleic acid comprising a sequence encoding a variable region sequence can be constructed from synthetic oligonucleotides (see e.g., Kolbinger, F., *Protein Engineering* 8:971–980 (1993)). A sequence encoding a signal peptide can also be incorporated into the nucleic acid (e.g., on synthesis, upon insertion into a vector). If the natural signal peptide sequence is unavailable, a signal peptide sequence from another antibody can be used (see, e.g., Kettleborough, C.A., *Protein Engineering* 4:773–783 (1991)). Using these methods, methods described herein or other suitable methods, variants can be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogengoom et al., WO 93/06213, published Apr. 1, 1993)).

Nucleic Acids and Constructs Comprising Same:

The invention also relates to isolated and/or recombinant (including, e.g., essentially pure) nucleic acids comprising sequences which encode a humanized immunoglobulin or humanized immunoglobulin light or heavy chain of the present invention.

Nucleic acids referred to herein as "isolated" are nucleic acids which have been separated away from the nucleic acids of the genomic DNA or cellular RNA of their source of origin (e.g., as it exists in cells or in a mixture of nucleic acids such as a library), and include nucleic acids obtained by methods described herein or other suitable methods, including essentially pure nucleic acids, nucleic acids produced by chemical synthesis, by combinations of biological and chemical methods, and recombinant nucleic acids which are isolated (see e.g., Daugherty, B. L. et al., *Nucleic Acids Res.,* 19(9): 2471–2476 (1991); Lewis, A. P. and J. S. Crowe, *Gene,* 101: 297–302 (1991)).

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector (e.g., plasmid) using restriction enzymes. "Recombinant" nucleic acids are also those that result from recombination events that occur through the natural mechanisms of cells, but are selected for after the introduction to the cells of nucleic acids designed to allow and make probable a desired recombination event.

The invention also relates more specifically to isolated and/or recombinant nucleic acids comprising a nucleotide sequence which encodes a humanized HF2.3D1 immunoglobulin, also referred to as humanized 3D1 (e.g., a humanized immunoglobulin of the invention in which the nonhuman portion is derived from the murine HF2.3D1 monoclonal antibody) or chain thereof. In one embodiment, the light chain comprises three complementarity determining regions derived from the light chain of the HF2.3D1 antibody, and the heavy chain comprises three complementarity determining regions derived from the heavy chain of the HF2.3D 1 antibody. Such nucleic acids include, for example, (a) a nucleic acid comprising a sequence which encodes a polypeptide comprising the amino acid sequence of the heavy chain variable region of a humanized HF2.3D1 immunoglobulin (e.g., SEQ ID NO: 5, See FIG. 2A), (b) a nucleic acid comprising a sequence which encodes a polypeptide comprising the amino acid sequence of the light chain variable region of a humanized HF2.3D1 immunoglobulin (e.g., SEQ ID NO: 7, See FIG. 2B), (c) a nucleic acid comprising a sequence which encodes at least a functional portion of the light or heavy chain variable region of a humanized HF2.3D1 immunoglobulin (e.g., a portion sufficient for antigen binding of a humanized immunoglobulin which comprises the chain). Due to the degeneracy of the genetic code, a variety of nucleic acids can be made which encode a selected polypeptide. In one embodiment, the nucleic acid comprises the nucleotide sequence of the variable region as set forth or substantially as set forth in FIG. 2A and/or FIG. 2B, including double or single-stranded polynucleotides. Isolated and/or recombinant nucleic acids meeting these criteria can comprise nucleic acids encoding sequences identical to sequences of humanized HF2.3D1 antibody or variants thereof, as discussed above.

Nucleic acids of the invention can be used in the production of humanized immunoglobulins having binding specificity for B7-2. For example, a nucleic acid (e.g., DNA) encoding a humanized immunoglobulin of the invention can be incorporated into a suitable construct (e.g., a vector) for further manipulation of sequences or for production of the encoded polypeptide in suitable host cells.

Method of Producing Humanized Immunoglobulins Having Specificity for B7-2:

Another aspect of the invention relates to a method of preparing a humanized immunoglobulin which has binding specificity for B7-2. The humanized immunoglobulin can be obtained, for example, by the expression of one or more recombinant nucleic acids encoding a humanized immunoglobulin having binding specificity for B7-2 in a suitable host cell.

Constructs or expression vectors suitable for the expression of a humanized immunoglobulin having binding specificity for B7-2 are also provided. The constructs can be introduced into a suitable host cell, and cells which express a humanized immunoglobulin of the invention, can be produced and maintained in culture. Suitable host cells can be procaryotic, including bacterial cells such as *E. coli, B. subtilis* and or other suitable bacteria, or eucaryotic, such as fungal or yeast cells (e.g., *Pichia pastoris, Aspergillus* species, *Saccharomyces cerevisiae, Schizosaccharomyces pombe, Neurospora crassa*), or other lower eucaryotic cells, and cells of higher eucaryotes such as those from insects (e.g., Sf9 insect cells (WO 94/26087, O'Connor, published Nov. 24, 1994)) or mammals (e.g., COS cells, NSO cells, SP2/0, Chinese hamster ovary cells (CHO), HuT 78 cells, 293 cells). (See, e.g., Ausubel, F. M. et al., eds. *Current Protocols in Molecular Biology*, Greene Publishing Associates and John Wiley & Sons Inc., (1993)).

Host cells which produce a humanized immunoglobulin having binding specificity for B7-2 can be produced as follows. For example, a nucleic acid encoding all or part of the coding sequence for the desired humanized immunoglobulin can be inserted into a nucleic acid vector, e.g., a DNA vector, such as a plasmid, virus or other suitable expression unit. A variety of vectors are available, including vectors which are maintained in single copy or multiple copy, or which become integrated into the host cell chromosome.

Suitable expression vectors can contain a number of components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence for membrane targeting or secretion. In a construct, a signal sequence can be provided by the vector or other source. For example, the transcriptional and/or translational signals of an immunoglobulin can be used to direct expression.

A promoter can be provided for expression in a suitable host cell. Promoters can be constitutive or inducible. For example, a promoter can be operably linked to a nucleic acid encoding a humanized immunoglobulin or immunoglobulin chain, such that it directs expression of the encoded polypeptide. A variety of suitable promoters for procaryotic (e.g., lac, tac, T3, T7 promoters for *E. coli*) and eucaryotic (e.g., yeast alcohol dehydrogenase (ADH1, SV40, CMV) hosts are available.

In addition, the expression vectors typically comprise a selectable marker for selection of host cells carrying the vector, and, in the case of replicable expression vector, an origin or replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The invention also relates to cells carrying these expression vectors.

For example, a nucleic acid (e.g., one or more nucleic acids) encoding the heavy and light chains of a humanized immunoglobulin having binding specificity for B7-2, or a construct (e.g., one or more constructs) comprising such nucleic acid(s), can be introduced into a suitable host cell by a method appropriate to the host cell selected (e.g., transformation, transfection, electroporation, infection), such that the nucleic acid(s) are operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded protein (e.g., humanized HF2.3D1 antibody) can be isolated from (e.g., the host cells, medium, milk). This process encompasses expression in a host cell of a transgenic animal (see e.g., WO 92/03918, GenPharm International, published Mar. 19, 1992).

Fusion proteins can be produced in which a humanized immunoglobulin or immunoglobulin chain is linked to a non-immunoglobulin moiety (e.g., a moiety which does not occur in immunoglobulins as found in nature) in an N-terminal location, C-terminal location or internal to the fusion protein. For example, some embodiments can be produced by the insertion of a nucleic acid encoding immunoglobulin sequences into a suitable expression vector, such as a pET vector (e.g., pET-15b, Novagen), a phage vector (e.g., pCANTAB 5 E, Pharmacia), or other vector (e.g., pRIT2T Protein A fusion vector, Pharmacia). The resulting construct can be introduced into a suitable host cell for expression. Upon expression, some fusion proteins can be isolated or purified from a cell lysate by means of a suitable affinity matrix (see e.g., *Current Protocols in Molecular Biology* (Ausubel, F. M. et al., eds., Vol. 2, Suppl. 26, pp. 16.4.1–16.7.8 (1991)).

Therapeutic Methods and Compositions:

Two types of T-cells exist: helper T cells and cytotoxic T cells. The helper T cells is a mechanism that can recognize the antigen when the antigen is coupled with a major histocompatibility complex (MHC). Antigen presenting cells internalize an antigen and re-express the antigen with the MHC molecule. Upon recognition of the antigen, a secretion of cytokines occur. Cytokine secretion activates B-lymphocytes and cytotoxic T cells, phagocytes and other cells. However, cytokine secretion and cellular proliferation require more than recognition of the antigen. Complete T-cell activation requires a second signal referred to as the "costimulatory signal." These costimulatory signals serve to initiate, maintain, and regulate the activation cascade. An important costimulatory pathway is called the B7:CD28/CTLA-4 pathway.

The B7:CD28/CTLA-4 pathway involves two costimulatory ligands, B7-1 (CD80) and B7-2 (CD86). The B7-1 and B7-2 ligands which are present on the antigen presenting cell each bind to two receptors on T-cells called CD28 and CTLA-4.

The expression of B7 antigens, B7-1 (CD80) and B7-2 (CD86), is tightly regulated. (Linsley, PS et al., Immunity 1:793–801 (1994). Unstimulated antigen-presenting cells generally do not express B7-1 and B7-2, except in dendritic cells. After activation, dendritic and epidermal Langerhans' cells, B cells, and macrophages up-regulate the expression of B7-2 and B7-1. Additionally, B7-2 can be expressed on granulocytes and on T-cell molecules, and B7-1 is expressed in fibroblasts and T-cell molecules.

In most immune responses, B7-2 is induced earlier than B7-1 and rises to higher levels. B7-2 also affects the production of interleukin-4 (IL-4) and the generation of type 2 helper cells. B7 molecules are also responsible for costimulating CD8 T cells in the absence of CD4 T cells which can be helpful in generating vaccines against melanoma. B7 molecules can costimulate natural killer cells and γ/δ T cells. Hence, modulation of B7 molecules is helpful in anti-tumor and anti-microbial immunity.

The B7:CD28/CTLA-4 pathway participates in various disease states including the pathogenesis of infectious diseases, asthma, autoimmune diseases, inflammatory disorders, the rejection of grafted organs and graft versus host disease. This pathway also participates in prophylaxis and mechanisms that stimulate the immune system. Transfection with genes encoding costimulators, such as B7, are applicable for anti-tumor and anti-viral vaccines. Also, the B7 molecules participate in autoimmune diseases such as systemic lupus erythematosus, diabetes mellitus, insulitis, arthritis, inflammatory bowel disease, inflammatory dermatitis (psoriasis vulgaris and atopic dermatitis), and multiple sclerosis. Reiser, Hans, M. D., et al., Mechanisms of Disease, New England J. of Med., Vol 335, No. 18, 1369 (1996).

Accordingly, the invention encompasses methods for treating the disease, as described herein, comprising administering immunoglobulin(s) that binds to B7-1 and/or B7-2. The immunoglobulin should be administered in therapeutically effective amounts and, optionally, in a carrier. In addition to the diseases described herein, the immunoglobulin that bind B7-1 and/or B7-2 can be administered to a person having transplanted tissue, organ or cells. Inhibiting the B7 pathway prevents or reduces the rejection of the transplanted tissue, organ or cell. The invention pertains to treating acute and/or chronic transplant rejection for a prolonged period of time (e.g., days, months, years).

Therefore, modulating or influencing the B7-2's role can be useful in treating patients with these diseases. B7-2 modulation is also useful in treating patients with immune-related or autoimmune diseases and disorders in which B7-2 participates. The modulation of B7-2 can also be used for diseases related to or affected by IL-4 and/or the generation of type 2 helper cells. These disorders/diseases can be treated using an antibody specific to B7-2. Preferably, the antibody is a humanized antibody specific to B7-2. Treatment of these diseases may be facilitated with co-administration of an anti-B 7-2 antibody, including chimeric and humanized versions thereof, with an anti-B7-1 antibody, or antibodies to the corresponding receptors, CD28 and CTLA-4. Methods of treatment also involve co-administration of a humanized anti B7-2 antibody or humanized anti B7-1 antibody with other standard therapy drugs, such methotrexate, cyclosporin, steroids, α CD40 ligands.

The invention includes methods for transplanting cells (e.g., blood cells or components, or bone marrow) to a patient in need thereof. A patient in need thereof is one, for example, having a disease that is treated with such a transplant (e.g., proliferative diseases such as leukemia, lymphoma, cancer), anemia such as sickle-cell anemia, thalassemia, and aplastic anemia) and myeloid dysplasia syndrome). The method comprises obtaining cells from a donor. Generally, donor bone marrow contains both immature and mature lymphocytes. The blood cells from a donor can be stem cells or immature blood cells in addition to bone marrow cells. The cells of the donor preferably comes from a person who has similar characteristics as the patient/recipient (e.g., the donor's bone marrow is a match to the patient's bone marrow). The characteristics that are analyzed to determine whether a donor is a match to the patient are MHC class 1 and 2 (e.g., HLA-A, HLA-B, and/or HLA-DR). The method involves contacting the cells (e.g., bone marrow or other blood components) with an immunoglobulin specific to B7-1 and/or an immunoglobulin specific to B7-2 and recipient cells (e.g., lymphocyte from the patient) to obtain a mixture (e.g., treated cells). The donor cells, immunoglobulin(s) and recipient cells are in contact for a period of time sufficient for tolerance induction (e.g., about 1–48 hours, preferably about 36 hours). Tolerance induction (e.g., anergy) refers to the lack of responsiveness to an antigen that has been induced with a treatment with B7-1 and/or B7-2 antibodies, such that the T-cell can no longer adequately or fully respond to that antigen. Example 9. The recipient cells (e.g., Peripheral Blood Lymphocytes (PBL), or lymphocytes that express class I antigens (MHC-I)) are radiated to prevent cells from dividing. A substitute for recipient cells can be tissue, organs or engineered cells that express MCH class I antigens, and B7-1 and/or B7-2 molecules. The method then includes introducing the mixture (e.g., treated cells) or bone marrow to the patient. This method of treatment is aimed at preventing graft vs. host disease. For example, cells in the treated bone marrow become tolerant to recipient alloantigen thereby reducing or eliminating graft vs. host disease. Accordingly, the claimed methods include treatment, preventing or aiding in the prevention of graft vs. host disease. The anti B7-1 and B7-2 antibodies reduce rejection of the donor bone marrow. However, the methods are able to reduce rejection without significantly compromising the patient's ability to detect and develop an immune response to other foreign cells and antigens. Hence, the methods allows the transplantation to be recipient specific and reject foreign antigens without compromising the transplant. See Exemplification Section.

The terms "pharmaceutically acceptable carrier" or a "carrier" refer to any generally acceptable excipient or drug delivery device that is relatively inert and non-toxic. A preferred embodiment is to administer the immunoglobulin, (e.g., tablet or capsule form). Exemplary carriers include calcium carbonate, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.), the teachings of which are incorporated herein by reference in their entirety.

Suitable carriers (e.g., pharmaceutical carriers) also include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the immunoglobulin. They can also be combined where desired with other active substances, e.g., enzyme inhibitors, to reduce metabolic degradation. A carrier (e.g., a pharmaceutically acceptable carrier) is preferred, but not necessary to administer the immunoglobulin.

For parenteral application, particularly suitable are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like. Ampules are convenient unit dosages.

Immunoglobulins of the invention can be administered intravenously, parenterally, intramuscular, subcutaneously, orally, nasally, by inhalation, by implant, by injection, or by suppository. The composition can be administered in a single dose or in more than one dose over a period of time to confer the desired effect.

The actual effective amounts of immunoglobulin can vary according to the specific immunoglobulin being utilized, the particular composition formulated, the mode of administration and the age, weight and condition of the patient, for example. As used herein, an effective amount of the immunoglobulin is an amount which modulates or inhibits B7 molecules. Dosages for a particular patient can be determined by one of ordinary skill in the art using conventional considerations, (e.g. by means of an appropriate, conventional pharmacological protocol).

The invention also pertains to methods for determining the presence, absence or level of B7-2 using a humanized anti-B7-2 antibody. The presence or absence of B7-2 can be detected in an assay (e.g., ELISA, radioimmunoassay (RIA) or FACS Immunohistochemistry). The assay can be a direct detection or an indirect detection (e.g. a competitive assay).

For example, to determine the presence or absence of B7-2 using an ELISA assay in a suitable sample, the method comprises combining a suitable sample with a composition comprising a humanized or murine anti B7-2 antibody as detector (e.g., biotinylated anti B7-2 MAb and HRP-streptavidin, or HRP-conjugated anti-B7-2 Mab) and a solid support (e.g., a microtiter plate), having an anti-B7-2 capture antibody bound (directly or indirectly) thereto. The detector antibody can bind to a different B7-2 epitope from that recognized by the capture antibody, under conditions suitable for the formation of a complex between the anti-B7-2 antibodies and B7-2. The method further comprises determining the formation of complex in the sample.

The presence of B7-2 can also be determined in a radioimmunoassay. For example, the presence of B7-2 can be assessed by an immunobinding assay comprising obtaining a sample, contacting the sample with a composition comprising an anti-B7-2 antibody (e.g., a humanized or murine anti-B7-2 antibody comprising a radioactive label; or a humanized or murine anti-B7-2 antibody comprising a binding site for a second antibody which comprises a radioactive label), preferably in an amount in excess of that required to bind the B7-2, under conditions suitable for the formation of labeled complexes. The method further comprises determining (detecting or measuring) the formation of complex in the samples.

EXEMPLIFICATION

The present invention will now be illustrated by the following Examples, which are not intended to be limiting in any way.

Example 1

Cloning and Sequencing of Mouse 3D1 Variable Region cDNAs

Mouse 3D1 (also referred to as HF2.3D1) heavy and light chain variable region cDNAs were cloned from mRNA isolated from hybridoma cells using anchored PCR (Co et al., *J. Immunol.* 148: 1149 (1992)). The 5' primers used annealed to the poly-dG tails added to the cDNA, and the 3' primers annealed to the constant regions. The amplified gene fragments were then inserted into the plasmid pUC18. Nucleotide sequences were determined from several independent clones for both $V_L$ and $V_H$ cDNA. For the heavy chain, a single, unique sequence was identified, typical of a mouse heavy chain variable region. For the light chain, two unique sequences, both homologous to murine light chain variable region sequences, were identified. However, one sequence was not functional because of a missing nucleotide that caused a frame shift at the V-J junction, and was identified as the non-productive allele. The other sequence was typical of a functional mouse kappa chain variable region. The variable region cDNA sequences of the heavy chain and the functional light chain and the translated amino acid sequences are shown in FIGS. 1A–1B. The mouse $V_L$ sequence belongs to Kabat's mouse kappa chain subgroup I. The mouse $V_H$ belongs to Kabat's heavy chain subgroup II(A).

Example 2

Design of Humanized 3D1 Variable Regions

To retain the binding affinity of the mouse antibody in the humanized antibody, the general procedures of Queen et al. were followed (Queen et al. *Proc. Natl.* Acad. Sci. USA 86:10029 (1989), U.S. Pat. Nos. 5,585,089 and 5,693,762, the teachings of which are incorporated herein in their entirety). The choice of framework residues can be critical in retaining high binding affinity. In principle, a framework sequence from any human antibody can serve as the template for CDR grafting; however, it has been demonstrated that straight CDR replacement into such a framework can lead to significant loss of binding affinity to the antigen (Tempest et al., *Biotechnology* 9:266 (1992); Shalaby et al., *J. Exp. Med.* 17: 217 (1992)). The more homologous a human antibody is to the original murine antibody, the less likely the human framework will introduce distortions into the mouse CDRs that could reduce affinity. Based on a sequence homology, III2R was selected to provide the framework for the humanized 3D1 heavy chain and H2F for the humanized 3D1 light chain variable region. Manheimer-Lory, A. et al., *J. Exp. Med.* 174(6):1639–52 (1991). Other highly homologous human antibody chains would also be suitable to provide the humanized antibody framework, especially kappa light chains from human subgroup 4 and heavy chains from human subgroup 1 as defined by Kabat.

Normally the heavy chain and light chain from the same human antibody are chosen to provide the framework sequences, so as to reduce the possibility of incompatibility in the assembling of the two chains. The III2R antibody shows a high homology to the 3D1 heavy and light chains and thus, was chosen to provide the framework for the initial humanized antibody model. The 3D1 light chain variable region, however, shows a significantly higher homology to the H2F framework compared to any others, including III2R. Therefore, H2F was chosen instead to provide the framework for the humanized 3D1 light chain variable region, while III2R was selected to provide the framework for the heavy chain variable region.

The computer programs ABMOD and ENCODE (Levitt et al., *J. Mol. Biol.* 168: 595 (1983)) were used to construct a molecular model of the 3D1 variable domain, which was used to locate the amino acids in the 3D1 framework that are close enough to the CDRs to potentially interact with them. To design the humanized 3D1 heavy and light chain variable regions, the CDRs from the mouse 3D1 heavy chain were grafted into the framework regions of the human III2R heavy chain and the CDRs from the mouse 3D1 light chain grafted into the framework regions of the human H2F light chain. At framework positions where the computer model suggested significant contact with the CDRs, the amino acids from the mouse antibody were substituted for the original human framework amino acids. For humanized 3D1, this was done at residues 27, 30, 48, 67, 68, 70 and 72 of the heavy chain and at residue 22 of the light chain. Furthermore, framework residues that occurred only rarely at their positions in the database of human antibodies were replaced by a human consensus amino acid at those positions. For humanized 3D1 this was done at residue 113 of the heavy chain and at residue 3 of the light chain.

The sequence of the humanized 3D1 antibody heavy chain and light chain variable regions is shown in FIGS. 2A–2B. However, many of the potential CDR-contact residues are amenable to substitutions of other amino acids that may still allow the antibody to retain substantial affinity to the antigen. Table 1 lists a number of positions in the framework where alternative amino acids may be suitable (LC=light chain, HU=heavy chain). The position specified in the table are the number of amino acids from the first amino acid of the mature chain, which is indicated by a double underline (FIGS. 2A–2B). For example, position LC-22 is the twenty second amino acid beginning from the doubled underlined Aspartic Acid, D, (or the forty second amino acid from the start codon).

TABLE 1

Complementarity Determining Region Amino Acids Substitutes and/or Alternatives

| Position | Humanized 3D1 | Alternatives |
|----------|---------------|--------------|
| LC-22 | S | N |
| HU-27 | Y | G |
| HU-30 | T | S |
| HU-48 | I | M |
| HU-67 | K | R |
| HU-68 | A | V |
| HU-70 | M | I |
| HU-72 | V | A |

Likewise, many of the framework residues not in contact with the CDRs in the humanized 3D1 heavy and light chains can accommodate substitutions of amino acids from the corresponding positions of III2R and H2F frameworks, from other human antibodies, from the mouse 3D1 antibody, or from other mouse antibodies, without significant loss of the affinity or non-immunogenicity of the humanized antibody. Table 2 lists a number of additional positions in the framework where alternative amino acids may be suitable.

TABLE 2

Framework Region Amino Acid Substitutes and/or Alternatives

| Position | Humanized 3D1 | Alternatives |
|----------|---------------|--------------|
| LC-3 | V | Q |
| HU-113 | T | I |

Selection of various alternative amino acids may be used to produce versions of humanized 3D1 that have varying combinations of affinity, specificity, non-immunogenicity, ease of manufacture, and other desirable properties. Thus, the examples in the above tables are offered by way of illustration, not of limitation.

Example 3

Construction of Humanized 3D1

Once the humanized variable region amino acid sequences had been designed, as described above, genes were constructed to encode them, including signal peptides, splice donor signals and appropriate restriction sites (FIGS. 2A–2B). The light and heavy chain variable region genes were constructed and amplified using eight overlapping synthetic oligonucleotides ranging in length from approximately 65 to 80 bases (see He et al. *J. Immunol.* 160: 1029 (1998)). The oligos were annealed pairwise and extended with the Klenow fragment of DNA polymerase I, yielding four double-stranded fragments. The resulting fragments were denatured, annealed, and extended with Klenow, yielding two fragments. These fragments were denatured, annealed pairwise, and extended once again, yielding a full-length gene. The resulting product was amplified by polymerase chain reaction (PCR) using Taq polymerase, gel-purified, digested with XbaI, gel-purified again, and subcloned into the XbaI site of the pVk for the expression of light chain and pVg4 or pVg2.M3 for the expression of heavy chains. The pVk vector for kappa light chain expression has been previously described (See Co et al., *J. Immunol.* 148:1149 (1992)). The pVg4 vector for the gamma 4 heavy chain expression was constructed by replacing the XbaI—BamHI fragment of pVg1 containing the g1 constant region gene (See Co et al., *J. Immunol.* 148: 1149 (1992)) with an approximately 2000 bp fragment of the human g4 constant region gene (Ellison and Hood, *Proc. Natl. Acad. Sci. USA* 79:1984 (1982)) that extended from the HindIII site preceding the $C_H1$ exon of the g4 gene to 270 bp after the NsiI site following the $C_H4$ exon of the gene. The pVg2.M3 vector for the gamma 2 heavy chain expression was described in Cole, et al., *J. Immunol.* 159: 3613 (1997). The pVg2.M3 is mutated from the human wildtype IgG2 by replacing the amino acids Val and Gly at positions 234 and 237 with Ala. This variant has a reduced interaction with its Fc receptors and thus has minimal antibody effector activity.

The structure of the final plasmids was verified by nucleotide sequencing and restriction mapping. All DNA manipulations were performed by standard methods well-known to those skilled in the art.

Two humanized 3D1, an IgG4 and an IgG2.M3, were generated for comparative studies. To construct a cell line producing humanized 3D1 (IgG4 or IgG2.M3), a light chain and the respective heavy chain plasmids were transfected into the mouse myeloma cell line Sp2/0-Ag14 (ATCC CRL 1581). Plasmids were also transfected into CHO cells using known methods in the art. Before transfection, the heavy and light chain-containing plasmids were linearized using restriction endonucleases. The kappa chain and the gamma2 chain were linearized using FspI; the gamma 4 chain was linearized using BstZ17I. Approximately 20 $\mu$g of the light chain and a heavy chain plasmid was transfected into $1\times10^7$ cells in PBS. Transfection was by electroporation using a Gene Pulser apparatus (BioRad) at 360 V and 25 $\mu$FD capacitance according to the manufacturer's instructions. The cells from each transfection were plated in four 96-well tissue culture plates, and after two days, selection medium (DMEM, 10% FCS, 1xHT supplement (Sigma), 0.25 mg/ml xanthine, 1 $\mu$g/ml mycophenolic acid) was applied.

After approximately two weeks, the clones that appeared were screened for antibody production by ELISA. Antibody from a high-producing clone was prepared by growing the cells to confluency in regular medium (DMEM with 10% FCS), then replacing the medium with a serum-free medium (Hybridoma SMF; Gibco) and culturing until maximum antibody titers were achieved in the culture. The culture supernatant was run through a protein A-Sepharose column (Pharmacia); antibody was eluted with 0.1 M Glycine, 100 mM NaCl, pH 3, neutralized and subsequently exchanged into phosphate-buffered saline (PBS). The purity of the antibody was verified by analyzing it on an acrylamide gel, and its concentration was determined by an $OD_{280}$ reading, assuming 1.0 mg of antibody protein has an $OD_{280}$ reading of 1.4.

Example 4

Affinity of Humanized Anti-B7-2 Antibody

Competitive Binding Assay

The relative affinities, of the murine and humanized 3D1 antibodies for the B7-2 antigen were determined by competitive binding assays. Three-fold serial dilutions of unlabelled humanized or murine 3D1 antibodies were mixed with a fixed amount of radio-iodinated murine 3D1 antibody (40,000–50,000 cpm per test in PBS containing 2% fetal calf serum).

$1\times10^5$ CHO cells expressing cell surface rhB7-2 (CHO/hB7-2) were added subsequently and the mixture (in a total volume of 200 ul) was incubated for 2 hr at 4° C. with gentle shaking. The cell-antibody suspension was then transferred to Sarstedt Micro Tubes (part #72.702) containing 100 ul 80% dibutyl phthalate-20% olive oil. After centrifugation in a microfuge, the Sarstedt tubes were plunged into dry ice for several minutes. Cell-bound $^{125}$I was determined by clipping tips of each tube (containing cell pellets) into scintillation vials and counting in a gamma counter. Bound and free counts were determined and the ratio plotted against the concentrations of the cold competitor antibodies according to the method of Berzofsky and Berkower (J. A. Berzofsky and I. J. Berkower, in Fundamental Immunology 9ed. W. E. Paul), Raven Press (New York), 595 (1984)).

Cell Line:

Recombinant Chinese Hamster Ovary (CHO) cell lines expressing hB7-2 on their membrane surfaces were cloned from cells transfected with B7-2 cDNA sequence and G418 resistance. Expression of hB7-2 on the CHO cell surface over many passages under selective pressure has been confirmed using murine anti-B7 antibodies and FACS analysis.

Preparation of $^{125}$I Labeled anti-hB7 mAb and Characterization:

Anti-hB7 antibodies were labeled with $^{125}$I by reaction with $^{125}$I-Bolton-Hunter reagent according to manufacturers instructions (Amersham Corp. Arlington Hts, Ill.). Protein was separated from free reagent with a NAP-25 column. An HPLC size-exclusion column was used to confirm that the antibodies remained intact and were not aggregated, and to measure protein concentration against standards prepared from non-labeled antibody. Labeling typically resulted in 4 to 8 microcuries per microgram of protein, or approximately 30 to 60% of the antibody molecules labeled.

Results:

The competitive binding graph is shown in FIG. 3. Each data point represents the average of triplicate determinations. Results showed that both humanized IgG4 and humanized IgG2.M3 anti-human B7-2 antibodies have a similar high binding affinity as the murine anti-human B7-2 antibody (approximately $1\times10^9$ $M^{-1}$), indicating no loss of affinity for B7-2 in the humanization of 3D 1. Both murine and humanized anti-B7-2 recognize cell surface expressed hB7-2 with high affinity.

Example 5

Direct Binding of Humanized Anti-B7 mAbs to CHO/hB7 Cells

Cell Binding Assay

Binding assays were begun by plating cells onto 96-well tissue culture plates at 10,000 CHO/hB7-2 cells per well. Two days later, adherent cells were gently washed with assay buffer containing nonfat dry milk protein (for blocking nonspecific binding) and sodium azide (to prevent internalization of antibodies by cells). For direct binding assays, $^{125}$I-labeled anti-B7 antibodies ($I^{125}$-murine anti-human B7-2; 826 cpm/fmol; humanized anti-human B7-2, 883 cpm/fmol) were serially diluted in assay buffer and incubated on cells overnight, allowing antibodies to bind to cell-surface B7 and come to equilibrium. Unbound antibody was gently washed from cells, and bound $^{125}$I-labeled antibody was detected using an $^{125}$I scintillant and photodetector system. Non-specific binding to CHO cells was determined for each dilution in the same manner, but on cells expressing the B7-1 molecule that is not recognized by the antibody being tested.

Figure 4:
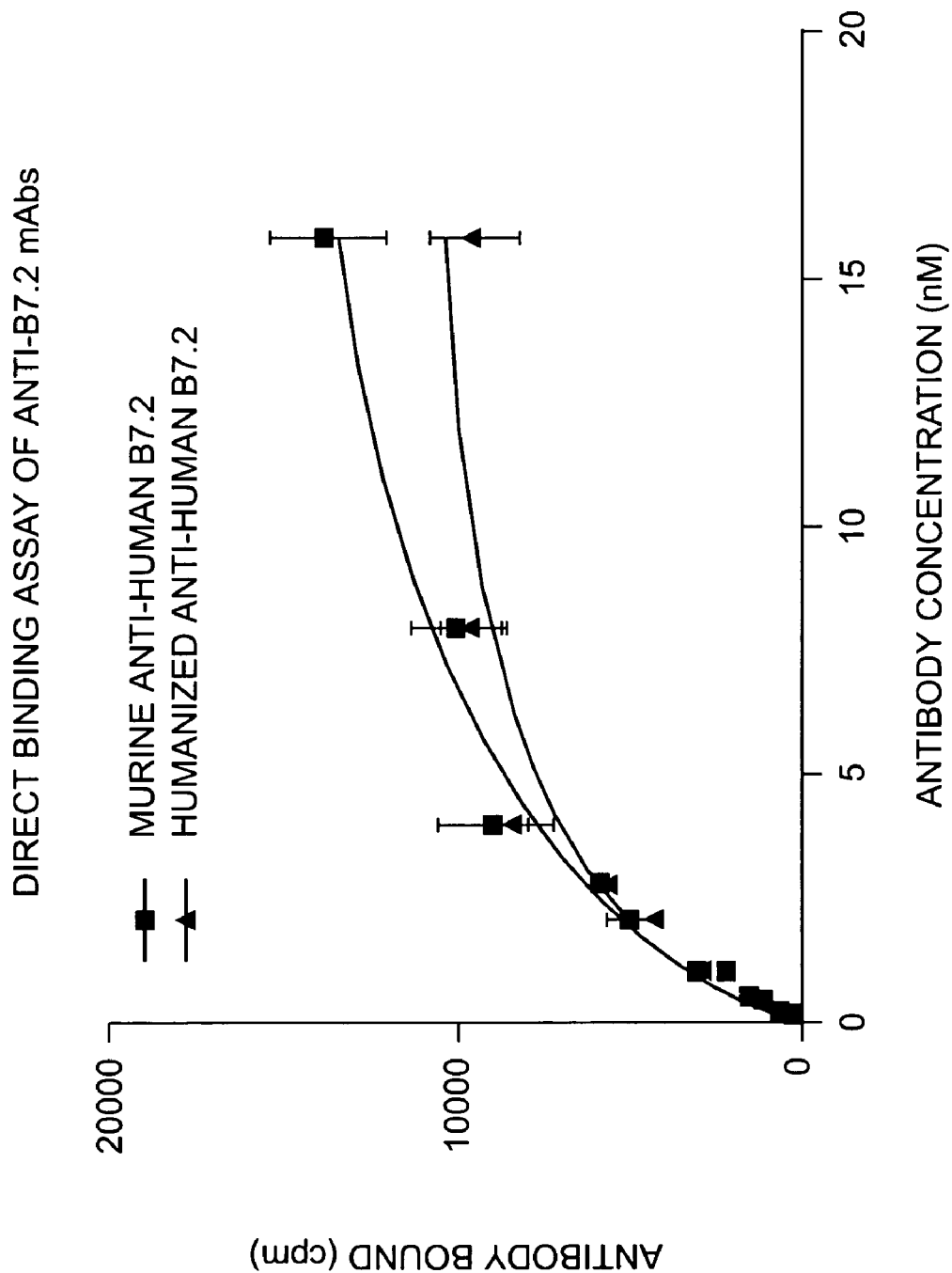
FIG. 4 is a graph depicting the results of a direct binding assay of murine or humanized anti-human B7-2 mAbs to CHO/hB7-2 cells. Increasing concentrations of radiolabelled antibodies were incubated with CHO or CHO/hB7-2 cells and the amount of specific antibody bound to the CHO/hB7-2 cells was determined.

Results:

The direct binding graph is shown in FIG. 4. The data, means of triplicate wells with nonspecific binding subtracted, were fit to a hyperbolic saturation curve using Graphpad PrismJ software. $K_D$ of the antibodies determined as the concentration corresponding to half-maximal binding indicated that the murine and humanized anti-B7-2 mAbs had similar and high binding affinities ($\sim10^{-9}$m) for B7-2. Both murine and humanized anti B7-2 antibodies recognize cell surface expressed hB7-2 with high affinity.

Example 6

Binding of Humanized Anti-B7 mAbs to Protein Ligands

Affinity Determination by BIACORE

The BIACORE biosensor (BIACORE; Uppsalla, Sweden) was used to determine binding kinetics of murine and humanized anti-B7-2 human antibodies to human hB7-2Ig. HB7-2Ig was immobilized onto the dextran matrix of a BIACORE sensor chip. Humanized and murine anti-human B7-2 were tested at 200, 100, 50, and 20 nM. Each dilution was tested 4 times per run and a total of three separate runs performed. Anti-human B7-2 antibody binding was measured in real time by Surface Plasmon Resonance (SPR) and global analysis was performed using the bivalent binding model in BIA evaluation software (version 3.1). For each sample, the association ($k_a$), dissociation ($k_d$), and equilibrium dissociation constant ($K_D$) were determined.

Results:

Table 3 reports the mean values obtained for both murine and humanized anti-human B7-2 mabs. The binding constants for the murine and humanized anti-B7-2 mAbs determined by SPR shows that the murine and humanized forms of the anti-B7-2 mAbs are similar and that the murine anti B7-2 mAb has a slightly higher binding constant for the immobilized hB7-2 Ig than does the humanized anti-B7-2. The approximately 2.8 fold higher affinity calculated for the murine anti-B7-2 mAb may represent a real, but slight difference between the murine and humanized anti B7-2 mAbs introduced during the humanization process. Another possibility may be due to technical variation in the preparation, processing and analysis of these antibodies. As shown in Examples 4, 5, and 7, a difference was not observed in humanized hB7-2 binding affinity in cell based assays.

TABLE 3

Affinity of anti-B7 mAbs as determined by BIAcore

| mAb | $K_D$ Humanized | $K_D$ Murine |
| --- | --- | --- |
| Anti-B7-2 | $5.1 \times 10^{-9}$M | $1.8 \times 10^{-9}$M |

Preparation of hB7-2 Ig:

A soluble form of hB7-2Ig was recovered from culture medium of CHO cells engineered to secrete this protein. Recombinant hB7-2Ig was derived by fusing the DNA coding sequences corresponding to the extracellular domain of B7-2 gene to the hinge-CH2-CH3 domains of the human IgG1 heavy chain. Recombinant hB7-2Ig was purified from the culture medium by protein A.

Example 7

Inhibition of T Cell Costimulation by Humanized anti-B7-2

CD28$^+$ Tcell/CH0-B7 Proliferation Assay

CD28$^+$ T cells, isolated as described herein, were washed once and resuspended in RPMI complete medium, supplemented with 2 ng/ml PMA (Calbiochem), to a cell density of $5\times10^5$ cells/ml. The CD28$^+$ T cells (100 ul, $5\times10^4$ cells) were added to the antibody/CHO/hB7-2 mixture (see below), incubated for 3 days at 37° C., 5% $CO_2$, and T cell proliferation was measured by pulsing for the last 6 hours of culture with 1 uCi of [$^3$H]-thymidine (NEN, Boston, Mass.). The cells were harvested on a filter and the incorporated radioactivity was measured in a scintillation counter.

Materials:

CD28$^+$ T cells were isolated by negative selection with immunoabsorption from human peripheral blood lymphocytes, as described (June et al., Mol. Cell. Biol. 7:4472–4481 (1987)). Buffy coats were obtained by leukophoresis of healthy human donors and peripheral blood lymphocytes (PBL) were isolated by density gradient centrifugation. Monocytes were depleted from the PBL by plastic absorption. CD28$^+$ T cells were isolated from the non-adherent cells by negative selection using antibodies to CD11, CD20, CD16 and CD 14, (this set of antibodies will coat all B cells, monocytes, large granular lymphocytes, and CD28$^-$ T cells) and magnetic bead separation using goat anti-mouse immunoglobulin-coated magnetic particles.

CHO/hB7-2 cells were detached from the tissue culture plates by incubation in phosphate-buffered saline without $Ca^{2+}$ and $Mg^+$ (PBS) with 0.5 mM EDTA and fixed with freshly prepared paraformaldehyde.

Various concentrations of anti-B7 antibody (in duplicate) were preincubated for 1 hour at 37° C., 5% $CO_2$ with $1 \times 10^4$ CHO/hB7-2 cells in 100 ul RPMI complete medium (RPMI 1640 medium, 10% fetal bovine serum (FBS),100 U/ml penicillin, 100 ug/ml streptomycin) in a microtiter plate (flat-bottom, 96-well, Costar, Cambridge, Mass.).

Figure 5:
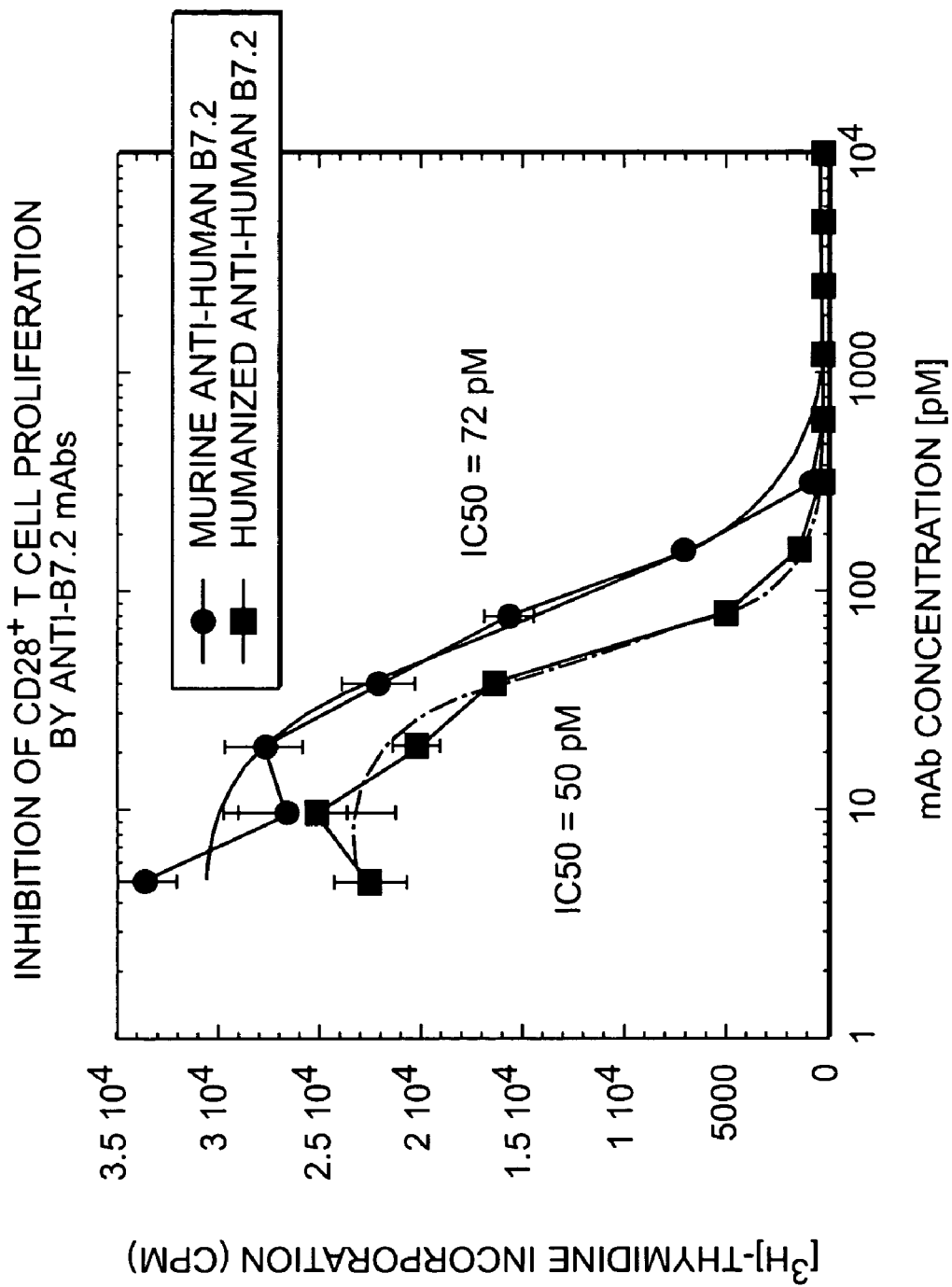
FIG. 5 is a graph depicting the results of a T cell proliferation assay. Increasing concentrations of murine or humanized anti-human B7-2 mAbs were added to CD28+ human T cells stimulated with PMA and CHO/hB7-2 cells and the inhibition of T cell proliferation by these mAbs was determined.

Results:

FIG. 5 shows the results of the inhibition of human $CD28^+$T cell proliferation by the murine and humanized anti-hB7-2 mAbs. Both antibodies exhibit dose dependent inhibition of B7-2 driven T cell proliferation with similar $IC_{50}$ (Inhibitory concentration 50%; amount of antibody required to inhibit the maximal T cell proliferation by 50%) values of 72 pm (murine anti-hB7-2) and 50 pm (humanized anti-hB 7-2) indicating that both antibodies were similar and very effective in inhibiting the B7-2 T cell stimulatory signal. This demonstrates that the high affinity anti B7-2 mAbs can block B7-2 functionality by inhibiting (e.g., preventing) the activation and/or proliferation of human T cells. These mAbs are expected to exhibit similar capability in in vivo use to inhibit T cell response.

Example 8

Inhibition of Mixed Lymphocyte Reactions by anti-B7-1 and anti-B7-2 mAbs

Mixed Lymphocyte Reactions (MLR):

Normal peripheral blood lymphocytes (PBL) (responders) were cultured with irradiated (2,500 cGy) normal donor PBL (stimulators) in RPMI 1640 containing 5% heat-inactivated human AB serum at 37° C. in 5% $CO_2$ at a final concentration of $10^6$ cells/mL. Where indicated, murine anti-hB7-1 or murine anti-hB7-2 antibodies were added alone (10 ug/mL), in combination (10 ug/mL each), and in comparison with CTLA4Ig (10 or 20 ug/mL). Cells were cultured in triplicate in microtiter plates in a final volume of 200 uL and proliferation was assessed by [$^3$H]-thymidine incorporation for the last 16 hours of culture. Secondary MLR was performed using the cells derived from the primary MLRs as responders. These cells were washed, cultured overnight, and restimulated as above using the same or different, third party stimulator PBLs. No inhibitors were added to the secondary MLRs.

Figure 6:
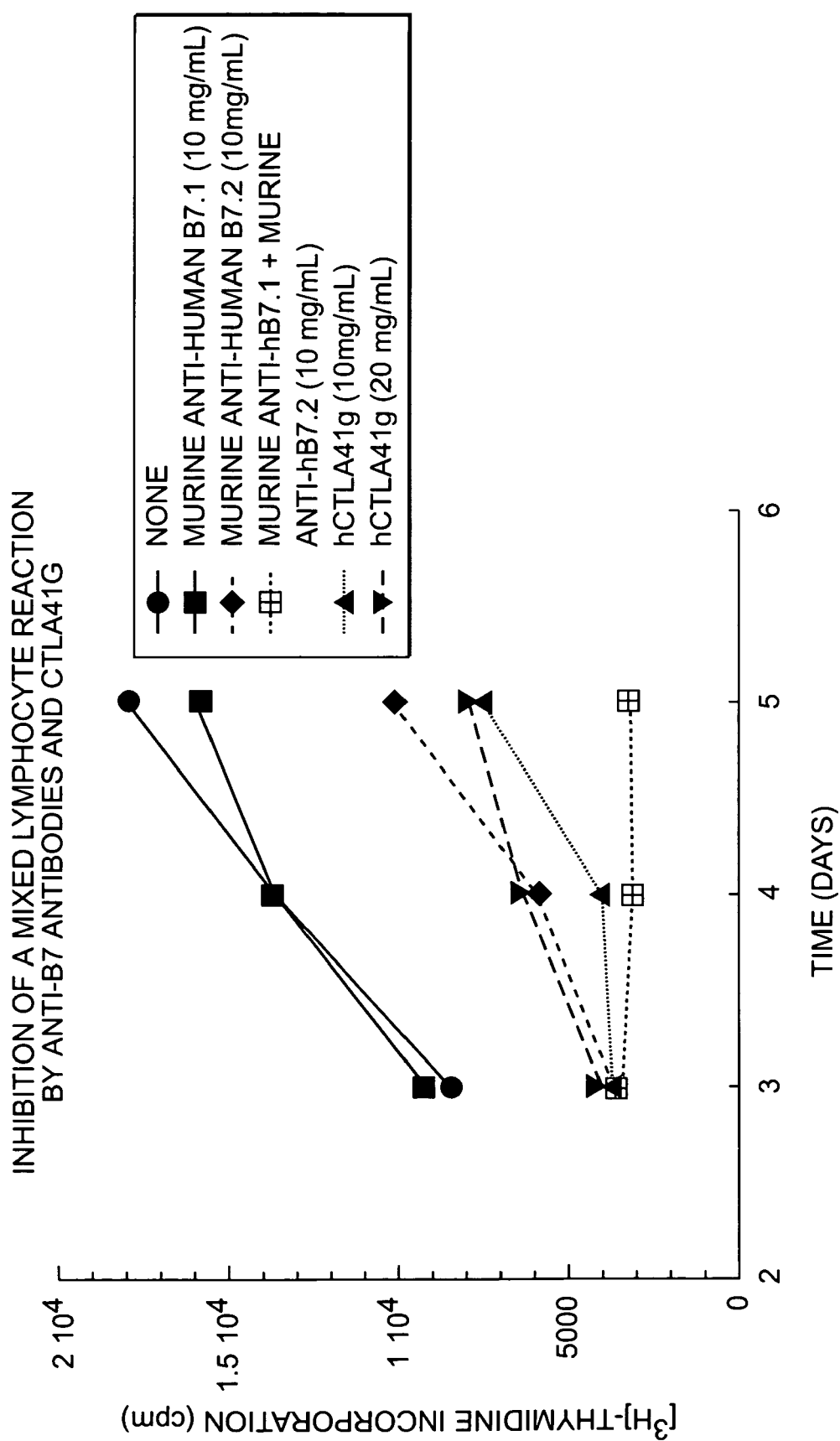
FIG. 6 is a graph depicting the results of a one way mixed lymphocyte reaction (MLR) assay. Fixed concentrations of murine or humanized anti-human B7-2 (IgG2.M3 isotype) or hCTLA4Ig were added to a mixture of human responder and stimulator PBLs and the proliferation of the responder PBLs was determined on days 3, 4, and 5 by the addition of radiolabelled thymidine.

Results:

The determinations shown in FIG. 6 were made by performing primary one-way MLRs in the absence or presence of B7 inhibitors (anti-B7, CTLA4Ig). The proliferation was measured after 3,4, or 5 days of culture.

In the primary MCR, the additional anti-B7-1 mAb alone had no inhibitory effect indicating a minor role for B7-1 alone in driving proliferation of responder T cells. Anti-B7-2 alone inhibited T cell proliferation on all days tested at a level comparable to hCTL4Ig, a recombinant protein known to bind to both B7-1 and B7-2. The combination of anti-B7-1 and anti-B7-2 was the most effective inhibitor of T cell proliferation that completely inhibited this response on all days tested. The superior ability of the combined anti-B7-1 and anti-B7-2 to inhibit T cell proliferation, as compared to hCTL4Ig, reflects the higher affinity of the anti-B7 mAbs for B7-1 and B7-2 as compared to hCTL4Ig. The combined anti-B7-1 and anti-B7-2 mAbs were better inhibitors of T cell proliferation than anti-B7-2 alone, demonstrating the need to block both stimulatory receptors to completely inhibit T cell responses. These results show that complete blockade of the B7-1 and B7-2 costimulators more completely abrogates alloresponsiveness in the MLR. Accordingly, these results indicate that methods of treatment including both anti B7-1 and anti B7-2 antibodies will be even more effective than either of the antibodies alone, especially where both costimulatory molecules are functional. While the responder/stimulator pair, described herein, was not sensitive to inhibition by anti-B7-1 alone, some responder/stimulator pairs do exhibit moderate (0–50%) anti-B7-1 sensitivity.

Figure 7:
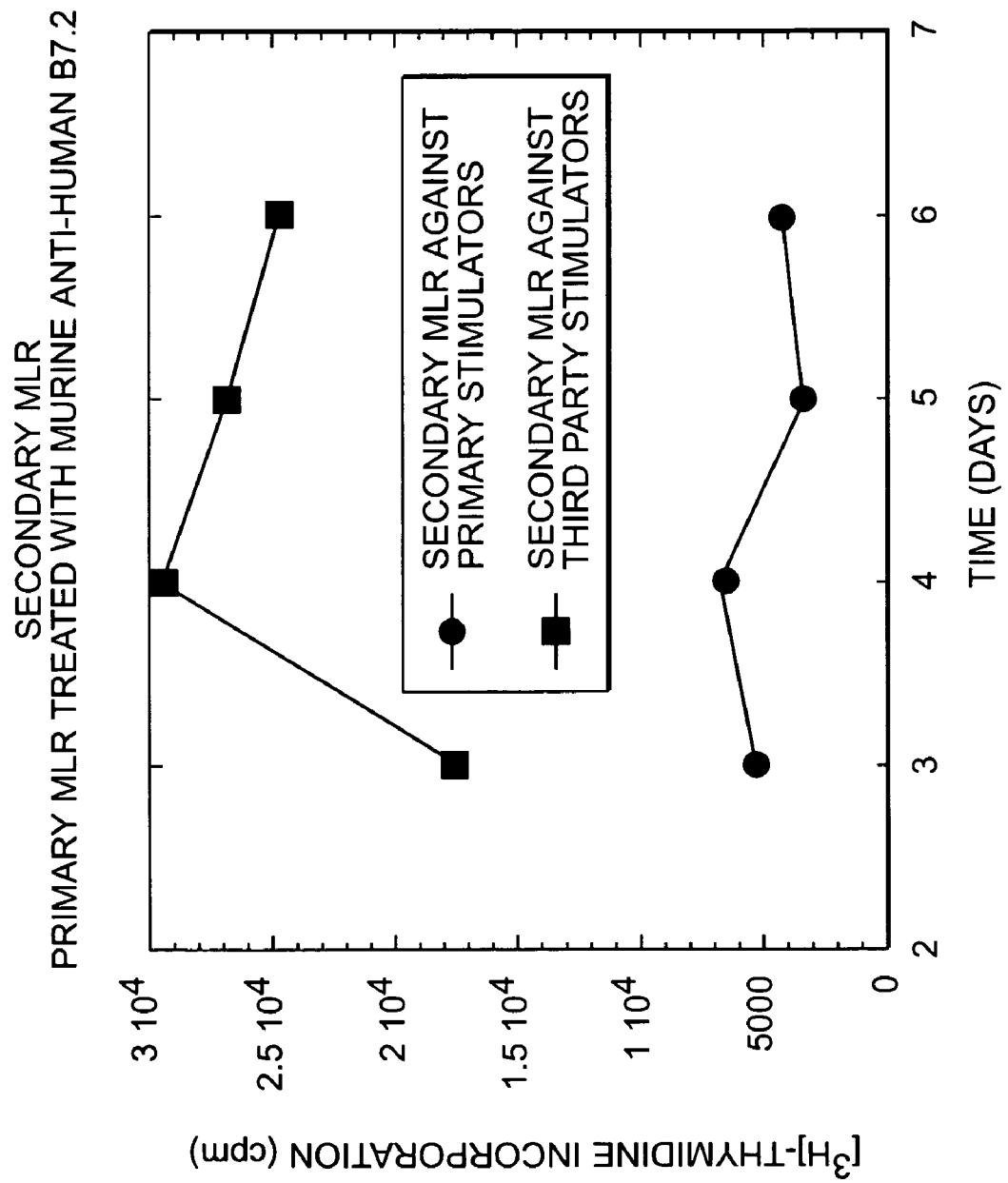
FIG. 7 is a graph depicting the results of a one way secondary MLR assay using PBLs from a primary MLR as responders and PBLs from the same or a different individual as in the primary MLR as stimulators. The humanized anti-human B7-2 mAb (IgG2.M3 isotype) was added to the primary MLR only. Proliferation of the responder PBLs in the secondary MLR was determined on days 3, 4, and 5 by the addition of radiolabelled thymidine.

To determine whether treatment with anti-B7 mAbs in the primary MLR had resulted in the development of T cell hyporesponsiveness or anergy, the responder T cells from the primary MLRs were tested in secondary MLRs where the stimulators were either from the same donor as the primary MLR or from a third party. The results in FIG. 7 show that the responder T cells from the primary MLR treated with anti-B7-2 alone failed to respond to the same stimulators as used in the primary MLR but retained normal proliferative response to third party, unrelated stimulators indicating that these responder T cells were rendered tolerant to the original stimulator PBLs by treatment with anti-B7-2 and that the toleraization was specific for the stimulator antigens present in the primary MLR. With this responder/stimulator pair, treatment with anti-B7-2 alone resulted in tolerance to the stimulator cells; however, with other responder/stimulator pairs, the induction of tolerance may not be complete.

Figure 8:
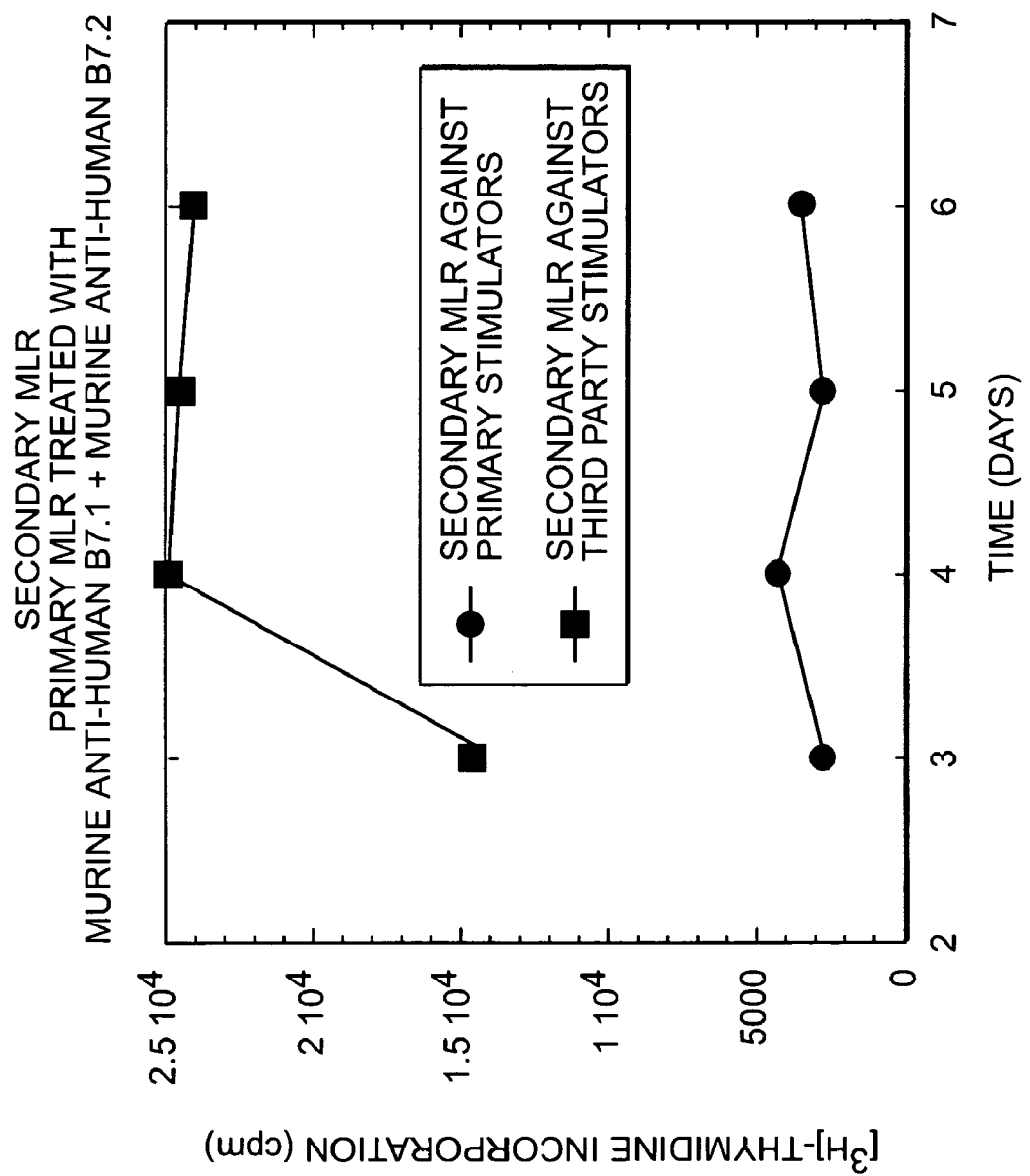
FIG. 8 is a graph depicting the results of a one way secondary MLR assay using PBLs from a primary MLR as responders and PBLs from the same or a different individual as in the primary MLR as stimulators. The humanized anti-human B7-1 and B7-2 mAbs (IgG2.M3 isotype) were added to the primary MLR only. Proliferation of the responder PBLs in the secondary MLR was determined on days 3, 4, and 5 by the addition of radiolabelled thymidine.

FIG. 8 shows that the responder T cells from the primary MLR treated with anti-B7-1 and anti-B7-2 failed to respond to the same stimulators as used in the primary MLR, but retained normal proliferative response to third party, unrelated stimulators. This indicates that these responder T cells were rendered tolerant to the original stimulator PBLs by treatment with the combined anti-B7-1 and anti-B7-2. The results obtained with this responder/stimulator pair are typical for other responder/stimulator pairs in that tolerance induction is the rule.

Example 9

Inhibition of Immune Responses in Non-Human Primates by Anti-B7 mAbs; Inhibition of Anti-Tetanus Responses Method:

Twelve tetanus naïve, 4–6 kg male cynomolgus macaques (macaca fasicularis) were divided into four experimental groups of three animal per group:

Group A; received 2 immunizations with 10 Lf Units (Flocculation Units) i.m. tetanus toxoid on day 0 and 42 (controls).

Group B; received 10 mg/kg of each humanized anti-B7.1 (1F1) and anti-B7.2 (3D1) i.v., at least 90 minutes before 10 Lf units i.m. tetanus toxoid on day 0; tetanus toxoid immunization only (without Ab pretreatment) on day 42 (Costimulation blockade with primary immunization).

Group C; received tetanus toxoid immunization only (without Ab pretreatment) on day 0; 10 mg/kg of each humanized anti-B7.1 and anti-B7.2 i.v., at least 90 minutes before 10 Lf units i.m. tetanus toxoid on day 42 (Costimulation blockade with secondary immunization).

Group D; received 10 mg/kg of each humanized anti-B7.1 (1F1) and anti-B7.2 (3D1) i.v., at least 90 minutes before 10 Lf units i.m. tetanus toxoid on day 0; received 10 mg/kg of each humanized anti-B7.1 and anti-B7.2 i.v., at least 90 minutes before 10 Lf units i.m. tetanus toxoid on day 42 (Costimulation blockade with primary and secondary immunization).

Serum samples for anti-tetanus antibody testing were collected on days 0, 7, 14, 21, 28, 35, 42, 49, 56, 63, 70, 77, and 84.

Anti-tetanus Antibody ELISA:

96-well ELISA plates were coated with tetanus toxoid lot TP-1002 at 4 ug/ml. A four-log titration of serum samples was performed starting at 1:100. Ab binding to tetanus was detected with a combination of monoclonal anti-human IgG and polyclonal goat anti-rhesus IgM HRP-conjugated antibodies, and developed with TNB substrate.

Figure 9:
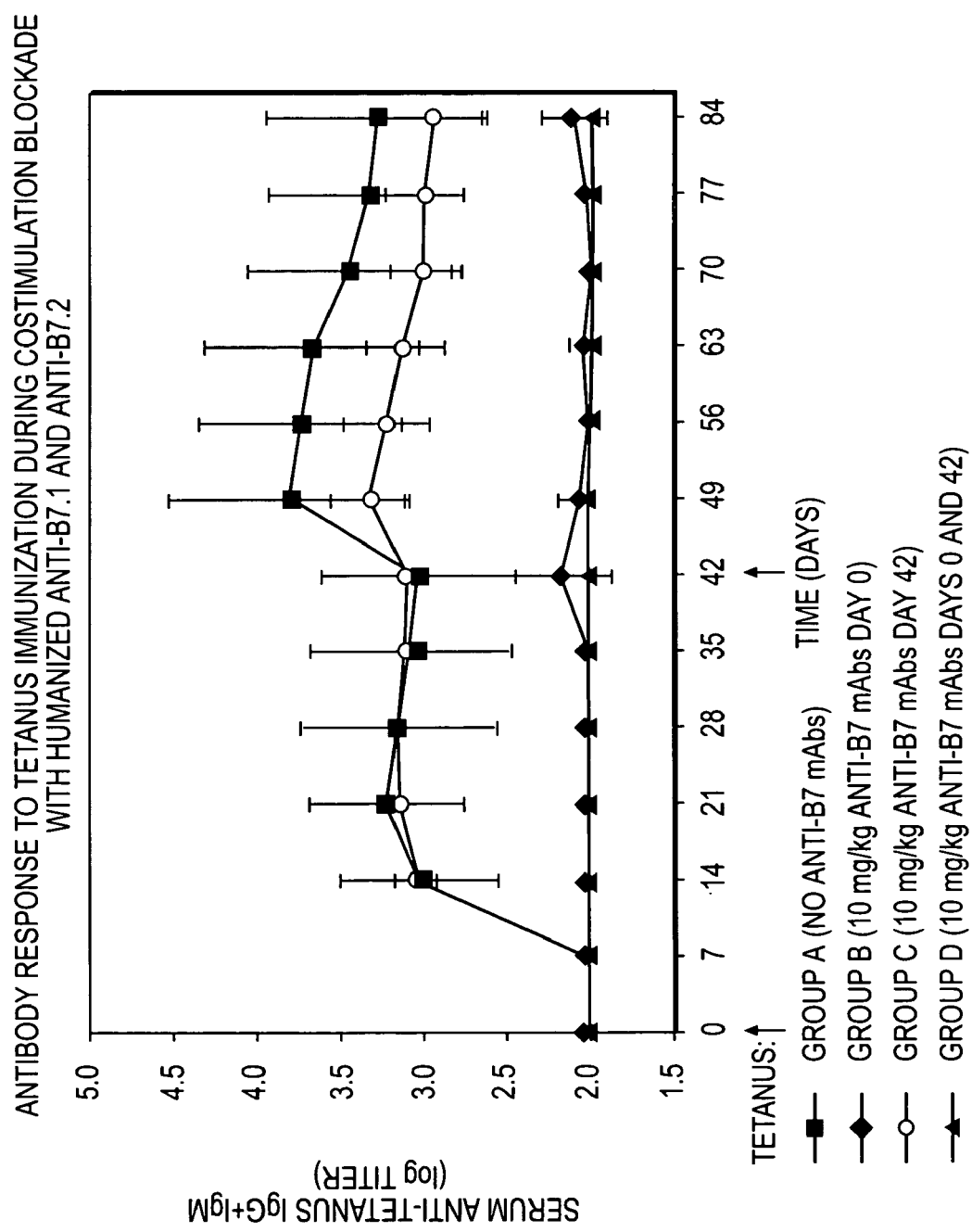
FIG. 9 is a graph depicting the anti-tetanus response in non-human primates immunized with tetanus toxoid. Cynomolgus monkeys were immunized with purified tetanus toxoid and treated with humanized anti-B7-1 and humanized anti-B7-2 (IgG2.M3 isotype) antibodies. Serum anti-tetanus antibody titers (IgM & IgG) were measured weekly over a 12 week period.

Results:

FIG. 9 shows the anti-tetanus IgM+IgG responses in monkeys immunized with tetanus toxoid and treated with the combined anti-B7-1 and anti-B7-2 mAbs.

Fourteen days after primary immunization, monkeys receiving tetanus toxoid only (Group A) had developed serum anti-tetanus antibody titers of log 3 to 3.5 indicating a normal immune response to the tetanus antigen. An increase anti-tetanus response was seen after the second tetanus immunization on day 42. Monkeys treated with the combination of anti-B7.1 and anti-B7.2 before both the primary and secondary immunization (Group D) lacked detectable antibody titers until at least day 84. Monkeys treated with anti-B7.1 and anti-B7.2 before the primary immunization only (Group B) maintained an undetectable anti-tetanus antibody titer until at least day 42, and a low (less than log 2.5) until at least day 84. Pretreatment with anti-B7.1 and anti-B7.2 before secondary tetanus immunization suppressed the secondary antibody response slightly (Group C vs. Group A). Therefore, the administration of anti-B7 antibodies concurrent with exposure to a new antigen (tetanus immunization) can prevent the development of a new antibody response and can lesson the strength of a secondary response to the same antigen. Since aspects of the rejection of transplanted organs and many autoimmune diseases involve the generation of antibody responses, treatment with humanized anti-B7 mAbs is useful in preventing organ rejection and in treating autoimmune diseases.

Example 10

Serum Half-Life of anti-B7 Antibodies in Non-Human Primates

The murine-anti-hB7-1 and murine-anti-hB7-2 mAbs were tested in non-human primates for serum half-life and target cell saturation. Three Cynomolgus monkeys were dosed with one dose each of a combination of the anti-hB7-1 and anti-hB7-2 mAbs at 2, 8, or 20 mg each mAb/kg body weight. The monkeys were analyzed for mAb binding to PBMC (Proliferative Blood Mononuclear Cells), serum mAb concentration, and primate anti-mouse antibody (PAMA) response (Table 6). PBMC saturation was determined by flow cytometry (FACS) where PBMCs isolated from the blood of mAb dosed primates were stained with goat-anti-murine Ig-PE (% in vivo) or the PBMC were first reacted with the anti-hB7-1 and anti-hB7-2 mAbs followed by detection with the goat-anti-murine Ig-PE (% ex vivo). The level of PBMC saturation at the various time points was calculated by (% in vivo/% ex vivo)×100. This study shows that PBMC saturation for the anti-hB7-1 and anti-B7-2 mAbs falls below 80% between days 4 to 6 (mAbs @ 2 mg/ks), days 6 to 8 (mAbs @ 8 mg/kg), and days 13 to 20 (mAbs @ 20 mg/kg) depending upon mAb dose. Although not measured directly, there was no apparent dramatic decrease in the numbers of circulating $B7^+$ cells.

Serum half-lives of the anti-hB7-1 and anti-hB7-2 mAbs was measured with a specific ELISA for each mAb using hB7-1Ig or hB7-2Ig as target and goat-anti-murine Ig HRP/ABTS for detection. These assays were sensitive to 400 ng/ml and 200 ng/ml for anti-hB7-2 and anti-hB17-1, respectively. PAMA responses were measured using a commercially available kit. The serum concentrations of the two anti-hB7 mAbs and the PAMA responses are shown at the individual dosage levels for each mAb. Both mAbs exhibit similar serum half lines of ~48 hours as determined at all three dosage levels. Increasing mAb dosage increased serum mAb concentrations by a comparable factor at all dosages and times tested. When dosed at 20 mg/kg, circulating mAb levels of >30 ug/ml were found for each mAb at 6 days post dosing.

PAMA responses to the anti-hB7-1 and anti-hB7-2 mAbs were low and were first measurable beginning 10 days after serum mAb levels had fallen below 10 ug/ml.

The serum half-life of humanized anti-human B7-2 was also determined in cynomolgus monkeys (n=6) dosed once with 10 mg/kg of humanized anti B7-2 antibody. Serum concentration was monitored by specific ELISA assay for each antibody using HRP-anti human IgG2 and ABTS.

Figure 10:
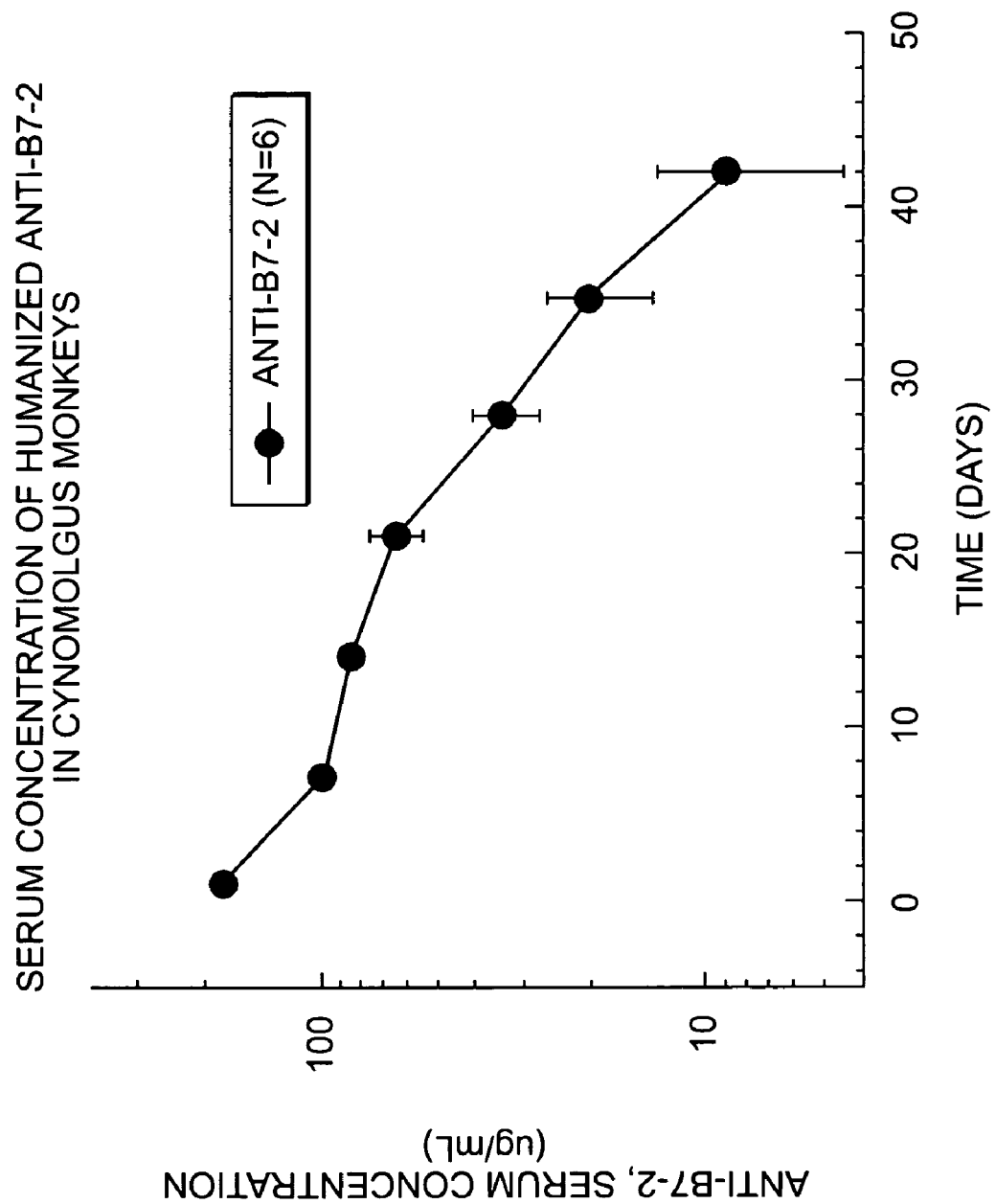
FIG. 10 is a graph showing the serum concentration of anti-B7-1 and anti-B7-2 (IgG2.M3 isotype) mAbs at various times after administration of an I.V. dose of 10 mg/Kg.

FIG. 10 shows the serum concentration of the humanized B7-2 mAb in cynomolgus monkeys during 42 days after dosing.

The humanized anti-human B7-2 mAb exhibited an extended serum half-life in cynomolgus monkeys as compared to a value of approximately 2 days for the murine anti-human B7-2 mAb when dosed at the same level, demonstrating that the humanized anti-human B7-2 mAb was retained in circulation much longer than the murine anti-B7-2 mAb.

TABLE 5

Results from the Preclinical primate studies

| Time Hours (Days) | Dose @ 2 mg each mAb/kg | | | Dose @ 8 mg mAb/kg | | | Dose @ 20 mg each mAb/kg | | |
|---|---|---|---|---|---|---|---|---|---|
| | Anti-hB7-2 ug/mL | PAMA ng/mL | PBL Saturation % | Anti-hB7-2 ug/mL | PAMA ng/mL | PBL Saturation % | Anti-hB7-2 ug/ml | PAMA ng/ml | PBL Saturation % |
| 0 .167 | BQL 61 | Neg. | 0 | BQL 206 | Neg. | 0 | BQL 580 | Neg. | 0 |

TABLE 5-continued

Results from the Preclinical primate studies

| Time Hours (Days) | Dose @ 2 mg each mAb/kg | | | Dose @ 8 mg mAb/kg | | | Dose @ 20 mg each mAb/kg | | |
|---|---|---|---|---|---|---|---|---|---|
| | Anti-hB7-2 ug/mL | PAMA ng/mL | PBL Saturation % | Anti-hB7-2 ug/mL | PAMA ng/mL | PBL Saturation % | Anti-hB7-2 ug/ml | PAMA ng/ml | PBL Saturation % |
| .5 | 59 | | 100 | 229 | | 25 | 570 | | 65 |
| 1 | 52 | | | 227 | | | 527 | | |
| 3 | 52 | | 100 | 230 | | 100 | 548 | | 100 |
| 5 | 50 | | | 139 | | | 464 | | |
| 8 | 44 | | | 169 | | | 412 | | |
| 24 (1D) | 26 | | 70 | 103 | | 100 | 286 | | 80 |
| 48 (2D) | 15 | | 100 | 59 | | 100 | 196 | | 100 |
| 96 (4D) | 2.4 | | 75 | 18 | | 100 | 83 | | 100 |
| 144 (6D) | BQL | | 95 | 3.9 | | 100 | 32 | | 100 |
| 192 (8D) | BQL | | 65 | BQL | | 100 | 13 | | 100 |
| 240 (10D) | BQL | | | BQL | | | 3.9 | | |
| 312 (13D) | BQL | Neg. | 5 | BQL | Neg. | 55 | BQL | Neg. | 80 |
| 480 (20D) | | 2908 | 10 | | 4080 | 10 | | 517 | 20 |
| 684 (27D) | | 1260 | | | 1460 | | | 1094 | |
| 816 (34D) | | | | | | | | | |

Example 11

Inhibition of Specific T-Cell Responses to Superantigens (Toxic Shock Syndrome Toxin-1; TSST-1)

NODscid mice were populated with human lymphocytes by the administration of 10e8 human PBLs. After 28 days, the mice were treated with TSST-1 (10 mg, I.P.) with or without the treatment with the combined antibodies to human B7-1 and B7-2 (500 mg, I.V.). After 14 additional days, the presence of human lymphocytes, T-cells, and TSST-1 specific T-cells (Vβ2-TCR-cells) in the peritoneal cavity was measured by FACS using antibodies specific for human CD45, CD4, and human Vβ2-TCR.

TABLE 6

| Addition | | Human T-cells (%) | |
|---|---|---|---|
| TSST-1 | Anti-B7-1 + anti-B7-2 | Total | Vβ2+ |
| − | − | 10.2 | 3.9 |
| + | − | 27.4 | 12.0 |
| + | + | 23.4 | 3.8 |

Results:
Tab le 6 shows the proportion of total human T cells and $V_\beta2^+$-TCR human T cells (TSST-1 specific) found in the peritoneal cavity of hu-NODscid mice. Treatment with TSST-1 greatly increased the percentage of human T cells and of TSST-1 specific human T cells ($V_\beta2^+$) in the huNOD-scid mice. Treatment with the anti-human B7-1 and B7-2 mAbs moderately diminished the total human T cell response and completely inhibited the expansion of the TSST-1 specific human T cells indicating that the anti-B-7 mAbs could effectively inhibit human T cell superantigen mediated responses.

The teachings of all the references, patents and/or patent applications cited herein are incorporated herein by reference in their entirety.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method for transplanting cells to a patient in need thereof, comprising:
   a) obtaining cells from a donor,
   b) obtaining recipient cells from the patient;
   c) contacting the donor cells with an immunoglobulin specific to B7-1 and an immunoglobulin specific to B7-2, wherein the immunoglobulin specific to B7-2 has a binding affinity of at least about $10^7 \text{M}^{-1}$, and wherein said immunoglobulin comprises an antigen binding region of non-human origin and at least a portion of an immunoglobulin of human origin, further wherein the antigen binding region of non-human origin comprises at least one framework region containing a substitution of at least one amino acid to a corresponding amino acid in the III2R heavy chain framework region or the H2F light chain framework region;
   d) combining b) and c) to form a mixture, and
   e) introducing the mixture of step d) to the patient.

2. The method of claim 1, wherein the cells from the donor are derived from bone marrow or blood.

3. The method of claim 2, wherein the recipient cell is a lymphocyte.

4. The method of claim 3, wherein the immunoglobulin specific to B7-1, and the immunoglobulin specific to B7-2 are in contact with the donor cells for a period of time between about 12 hours and 48 hours.

5. The method of claim 4, wherein the period of time is about 36 hours.

6. The method of claim 1, wherein the patient has a disease that is selected from the group consisting of: a proliferative disease, anemia and myeloid dysplasia syndrome.

7. The method of claim 6, wherein the proliferative disease is selected from the group consisting of: leukemia, lymphoma and cancer.

8. The method of claim 6, wherein the anemia is selected from the group consisting of: sickle-cell anemia, thalassemia and aplastic anemia.

9. The method of claim 1, wherein the immunoglobulin specific to B7-1 and the immunoglobulin specific to B7-2 are humanized.

10. The method of claim 1, wherein the immunoglobulin specific to B7-1 and the immunoglobulin specific to B7-2 are in contact with the donor cells for a period of time between about 1 hour and 48 hours.

11. The method of claim 1, wherein the immunoglobulin specific to B7-2 can compete with the murine antibody 3D1 (SEQ ID NOS: 2 and 4) for binding to B7-2.

12. The method of claim 1, wherein the immunoglobulin specific to B7-2 is derived from the cell line deposited with the ATCC, Accession No. CRL-12524.

13. A method for transplanting cells to a patient in need thereof, comprising:
  a) obtaining cells from a donor,
  b) obtaining a tissue, an organ, or recipient cells from the patient,
  c) contacting the donor cells with an immunoglobulin specific to B7-1 and an immunoglobulin specific to B7-2, wherein the immunoglobulin specific to B7-2 has a binding affinity of at least about $10^7 \, M^{-1}$, and wherein said immunoglobulin comprises an antigen binding region of non-human origin and at least a portion of an immunoglobulin of human origin, further wherein the antigen binding region of non-human origin comprises at least one framework region containing a substitution of at least one amino acid to a corresponding amino acid in the III2R heavy chain framework region or the H2F light chain framework region;
  d) combining b) and c) to form a mixture, and
  e) introducing the mixture of step d) to the patient.

14. The method of claim 13, wherein the cells derived from the donor are derived from bone marrow, stem cells or immature blood cells.

15. The method of claim 13, wherein the immunoglobulin specific to B7-1 and the immunoglobulin specific to B7-2 are in contact with the donor cells for a period of time between about 1 hour and 48 hours.

16. The method of claim 13, wherein the immunoglobulin specific to B7-1 and the immunoglobulin specific to B7-2 are humanized.

17. The method of claim 13, wherein the immunoglobulin specific to B7-2 can compete with the murine antibody 3D1 (SEQ ID NOS: 2 and 4) for binding to B7-2.

18. The method of claim 13, wherein the immunoglobulin specific to B7-2 is derived from the cell line deposited with the ATCC, Accession No. CRL-12524.

* * * * *

SEQUENCE LISTING

<160> NUMBER OF SEQ ID NOS: 20

<210> SEQ ID NO 1
<211> LENGTH: 405
<212> TYPE: DNA
<213> ORGANISM: Murine anti-B7-2 heavy chain

```
-continued

<220> FEATURE:
<221> NAME/KEY: CDS
<222> LOCATION: (1)...(405)
<223> OTHER INFORMATION:

<400> SEQUENCE: 1 atg ggt tgg aac tgt atc atc ttc ttt ctg gtt aca aca gct aca ggt      48
Met Gly Trp Asn Cys Ile Ile Phe Phe Leu Val Thr Thr Ala Thr Gly
1               5                   10                  15 gtg cac tcc cag gtc cag ctg cag cag tct ggg cct gag ctg gtg agg      96
Val His Ser Gln Val Gln Leu Gln Gln Ser Gly Pro Glu Leu Val Arg
                20                  25                  30 cct ggg gaa tca gtg aag att tcc tgc aag ggt tcc ggc tac aca ttc     144
Pro Gly Glu Ser Val Lys Ile Ser Cys Lys Gly Ser Gly Tyr Thr Phe
            35                  40                  45 act gat tat gct ata cag tgg gtg aag cag agt cat gca aag agt cta     192
Thr Asp Tyr Ala Ile Gln Trp Val Lys Gln Ser His Ala Lys Ser Leu
        50                  55                  60 gag tgg att gga gtt att aat att tac tat gat aat aca aac tac aac     240
Glu Trp Ile Gly Val Ile Asn Ile Tyr Tyr Asp Asn Thr Asn Tyr Asn
65                  70                  75                  80 cag aag ttt aag ggc aag gcc aca atg act gta gac aaa tcc tcc agc     288
Gln Lys Phe Lys Gly Lys Ala Thr Met Thr Val Asp Lys Ser Ser Ser
                85                  90                  95 aca gcc tat atg gaa ctt gcc aga ttg aca tct gag gat tct gcc atc     336
Thr Ala Tyr Met Glu Leu Ala Arg Leu Thr Ser Glu Asp Ser Ala Ile
                100                 105                 110 tat tac tgt gca aga gcg gcc tgg tat atg gac tac tgg ggt caa gga     384
Tyr Tyr Cys Ala Arg Ala Ala Trp Tyr Met Asp Tyr Trp Gly Gln Gly
            115                 120                 125 acc tca gtc acc gtc tcc tca                                         405
Thr Ser Val Thr Val Ser Ser
        130                 135

<210> SEQ ID NO 2
<211> LENGTH: 135
<212> TYPE: PRT
<213> ORGANISM: Murine anti-B7-2 heavy chain

<400> SEQUENCE: 2

Met Gly Trp Asn Cys Ile Ile Phe Phe Leu Val Thr Thr Ala Thr Gly
1               5                   10                  15

Val His Ser Gln Val Gln Leu Gln Gln Ser Gly Pro Glu Leu Val Arg
                20                  25                  30

Pro Gly Glu Ser Val Lys Ile Ser Cys Lys Gly Ser Gly Tyr Thr Phe
            35                  40                  45

Thr Asp Tyr Ala Ile Gln Trp Val Lys Gln Ser His Ala Lys Ser Leu
        50                  55                  60

Glu Trp Ile Gly Val Ile Asn Ile Tyr Tyr Asp Asn Thr Asn Tyr Asn
65                  70                  75                  80

Gln Lys Phe Lys Gly Lys Ala Thr Met Thr Val Asp Lys Ser Ser Ser
                85                  90                  95

Thr Ala Tyr Met Glu Leu Ala Arg Leu Thr Ser Glu Asp Ser Ala Ile
                100                 105                 110

Tyr Tyr Cys Ala Arg Ala Ala Trp Tyr Met Asp Tyr Trp Gly Gln Gly
            115                 120                 125

Thr Ser Val Thr Val Ser Ser
        130                 135
```

```
<210> SEQ ID NO 3
<211> LENGTH: 396
<212> TYPE: DNA
<213> ORGANISM: Murine anti-B7-2 light chain
<220> FEATURE:
<221> NAME/KEY: CDS
<222> LOCATION: (1)...(396)

<400> SEQUENCE: 3 atg gat tca cag gcc cag gtt ctt ata ttg ctg ctg cta tgg gta tct        48
Met Asp Ser Gln Ala Gln Val Leu Ile Leu Leu Leu Leu Trp Val Ser
 1               5                  10                  15 ggt acc tgt ggg gac att gtg ctg tca cag tct cca tcc tcc ctg gct        96
Gly Thr Cys Gly Asp Ile Val Leu Ser Gln Ser Pro Ser Ser Leu Ala
                20                  25                  30 gtg tca gca gga gag aag gtc act atg agc tgc aaa tcc agt cag agt       144
Val Ser Ala Gly Glu Lys Val Thr Met Ser Cys Lys Ser Ser Gln Ser
            35                  40                  45 ctg ctc aac agt aga acc cga gag aac tac ttg gct tgg tac cag cag       192
Leu Leu Asn Ser Arg Thr Arg Glu Asn Tyr Leu Ala Trp Tyr Gln Gln
        50                  55                  60 aaa cca ggg cag tct cct aaa ctg ctg atc tac tgg gca tcc act agg       240
Lys Pro Gly Gln Ser Pro Lys Leu Leu Ile Tyr Trp Ala Ser Thr Arg
 65                  70                  75                  80 gaa tct ggg gtc cct gat cgc ttc aca ggc agt gga tct ggg aca gat       288
Glu Ser Gly Val Pro Asp Arg Phe Thr Gly Ser Gly Ser Gly Thr Asp
                85                  90                  95 ttc act ctc acc atc agc agt gtg cag gct gaa gac ctg gca gtt tat       336
Phe Thr Leu Thr Ile Ser Ser Val Gln Ala Glu Asp Leu Ala Val Tyr
               100                 105                 110 tac tgc acg caa tct tat aat ctt tac acg ttc gga ggg ggg acc aag       384
Tyr Cys Thr Gln Ser Tyr Asn Leu Tyr Thr Phe Gly Gly Gly Thr Lys
           115                 120                 125 ctg gaa ata aaa                                                        396
Leu Glu Ile Lys
       130

<210> SEQ ID NO 4
<211> LENGTH: 132
<212> TYPE: PRT
<213> ORGANISM: Murine anti-B7-2 light chain

<400> SEQUENCE: 4

Met Asp Ser Gln Ala Gln Val Leu Ile Leu Leu Leu Leu Trp Val Ser
 1               5                  10                  15

Gly Thr Cys Gly Asp Ile Val Leu Ser Gln Ser Pro Ser Ser Leu Ala
                20                  25                  30

Val Ser Ala Gly Glu Lys Val Thr Met Ser Cys Lys Ser Ser Gln Ser
            35                  40                  45

Leu Leu Asn Ser Arg Thr Arg Glu Asn Tyr Leu Ala Trp Tyr Gln Gln
        50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
               100                 105                 110
```

Tyr Cys Thr Gln Ser Tyr Asn Leu Tyr Thr Phe Gly Gly Gly Thr Lys
        115                 120                 125

Leu Glu Ile Lys
    130

<210> SEQ ID NO 5
<211> LENGTH: 405
<212> TYPE: DNA
<213> ORGANISM: Humanized murine anti-human B7-2 heavy chain
<220> FEATURE:
<221> NAME/KEY: CDS
<222> LOCATION: (1)...(405)

<400> SEQUENCE: 5

| | |
|---|---|
| atg ggt tgg aac tgt atc atc ttc ttt ctg gtt acc aca gct aca ggt<br>Met Gly Trp Asn Cys Ile Ile Phe Phe Leu Val Thr Thr Ala Thr Gly<br>1               5                   10                  15 | 48 |
| gtg cac tcc cag gtc cag ctg gtg cag tct ggg gct gag gtg aag aag<br>Val His Ser Gln Val Gln Leu Val Gln Ser Gly Ala Glu Val Lys Lys<br>            20                  25                  30 | 96 |
| cct ggg agc tca gtg aag gtg tcc tgc aaa gct tcc ggc tac aca ttc<br>Pro Gly Ser Ser Val Lys Val Ser Cys Lys Ala Ser Gly Tyr Thr Phe<br>        35                  40                  45 | 144 |
| act gat tat gct ata cag tgg gtg aga cag gct cct gga cag ggc ctc<br>Thr Asp Tyr Ala Ile Gln Trp Val Arg Gln Ala Pro Gly Gln Gly Leu<br>    50                  55                  60 | 192 |
| gag tgg att gga gtt att aat att tac tat gat aat aca aac tac aac<br>Glu Trp Ile Gly Val Ile Asn Ile Tyr Tyr Asp Asn Thr Asn Tyr Asn<br>65                  70                  75                  80 | 240 |
| cag aag ttt aag ggc aag gcc aca atg act gta gac aag tcg acg agc<br>Gln Lys Phe Lys Gly Lys Ala Thr Met Thr Val Asp Lys Ser Thr Ser<br>                85                  90                  95 | 288 |
| aca gcc tat atg gaa ctt agt tct ttg aga tct gag gat acg gcc gtt<br>Thr Ala Tyr Met Glu Leu Ser Ser Leu Arg Ser Glu Asp Thr Ala Val<br>            100                 105                 110 | 336 |
| tat tac tgt gca aga gcg gcc tgg tat atg gac tac tgg ggt caa ggt<br>Tyr Tyr Cys Ala Arg Ala Ala Trp Tyr Met Asp Tyr Trp Gly Gln Gly<br>        115                 120                 125 | 384 |
| acc ctt gtc acc gtc tcc tca<br>Thr Leu Val Thr Val Ser Ser<br>    130                 135 | 405 |

<210> SEQ ID NO 6
<211> LENGTH: 135
<212> TYPE: PRT
<213> ORGANISM: Humanized murine anti-human B7-2 heavy chain

<400> SEQUENCE: 6

Met Gly Trp Asn Cys Ile Ile Phe Phe Leu Val Thr Thr Ala Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Ala Ile Gln Trp Val Arg Gln Ala Pro Gly Gln Gly Leu
    50                  55                  60

Glu Trp Ile Gly Val Ile Asn Ile Tyr Tyr Asp Asn Thr Asn Tyr Asn
65                  70                  75                  80

Gln Lys Phe Lys Gly Lys Ala Thr Met Thr Val Asp Lys Ser Thr Ser
                85                  90                  95

```
Thr Ala Tyr Met Glu Leu Ser Ser Leu Arg Ser Glu Asp Thr Ala Val
            100                 105                 110
Tyr Tyr Cys Ala Arg Ala Ala Trp Tyr Met Asp Tyr Trp Gly Gln Gly
        115                 120                 125
Thr Leu Val Thr Val Ser Ser
    130                 135

<210> SEQ ID NO 7
<211> LENGTH: 396
<212> TYPE: DNA
<213> ORGANISM: Humanized murine anti-human B7-2 light chain
<220> FEATURE:
<221> NAME/KEY: CDS
<222> LOCATION: (1)...(396)

<400> SEQUENCE: 7 atg gat tca cag gcc cag gtt ctt ata ttg ctg ctg cta tgg gta tct        48
Met Asp Ser Gln Ala Gln Val Leu Ile Leu Leu Leu Leu Trp Val Ser
 1               5                  10                  15 ggc acc tgt ggg gac att gtg ctg aca cag tct cca gat tcc ctg gct        96
Gly Thr Cys Gly Asp Ile Val Leu Thr Gln Ser Pro Asp Ser Leu Ala
            20                  25                  30 gta agc tta gga gag agg gcc act att agc tgc aaa tcc agt cag agt       144
Val Ser Leu Gly Glu Arg Ala Thr Ile Ser Cys Lys Ser Ser Gln Ser
        35                  40                  45 ctg ctc aac agt aga acc cga gag aac tac ttg gct tgg tac cag cag       192
Leu Leu Asn Ser Arg Thr Arg Glu Asn Tyr Leu Ala Trp Tyr Gln Gln
    50                  55                  60 aaa cca ggg cag cct cct aaa ctg ctg atc tac tgg gca tcc act agg       240
Lys Pro Gly Gln Pro Pro Lys Leu Leu Ile Tyr Trp Ala Ser Thr Arg
 65                  70                  75                  80 gaa tct ggg gtc cct gat cgc ttc agt ggc agt gga tct ggg aca gat       288
Glu Ser Gly Val Pro Asp Arg Phe Ser Gly Ser Gly Ser Gly Thr Asp
                 85                  90                  95 ttc act ctc acc atc agc agt ctg cag gct gaa gac gtg gca gtt tat       336
Phe Thr Leu Thr Ile Ser Ser Leu Gln Ala Glu Asp Val Ala Val Tyr
            100                 105                 110 tac tgc acg caa tct tat aat ctt tac acg ttc gga cag ggg acc aag       384
Tyr Cys Thr Gln Ser Tyr Asn Leu Tyr Thr Phe Gly Gln Gly Thr Lys
        115                 120                 125 gtg gaa ata aaa                                                       396
Val Glu Ile Lys
    130

<210> SEQ ID NO 8
<211> LENGTH: 132
<212> TYPE: PRT
<213> ORGANISM: Humanized murine anti-human B7-2 light chain

<400> SEQUENCE: 8

Met Asp Ser Gln Ala Gln Val Leu Ile Leu Leu Leu Leu Trp Val Ser
 1               5                  10                  15

Gly Thr Cys Gly Asp Ile Val Leu Thr Gln Ser Pro Asp Ser Leu Ala
            20                  25                  30

Val Ser Leu Gly Glu Arg Ala Thr Ile Ser Cys Lys Ser Ser Gln Ser
        35                  40                  45

Leu Leu Asn Ser Arg Thr Arg Glu Asn Tyr Leu Ala Trp Tyr Gln Gln
    50                  55                  60

Lys Pro Gly Gln Pro Pro Lys Leu Leu Ile Tyr Trp Ala Ser Thr Arg
 65                  70                  75                  80
```

```
                Glu Ser Gly Val Pro Asp Arg Phe Ser Gly Ser Gly Ser Gly Thr Asp
                                85                  90                  95

Phe Thr Leu Thr Ile Ser Ser Leu Gln Ala Glu Asp Val Ala Val Tyr
                            100                 105                 110

Tyr Cys Thr Gln Ser Tyr Asn Leu Tyr Thr Phe Gly Gln Gly Thr Lys
                        115                 120                 125

Val Glu Ile Lys
                    130

<210> SEQ ID NO 9
<211> LENGTH: 15
<212> TYPE: DNA
<213> ORGANISM: Artificial Sequence
<220> FEATURE:
<223> OTHER INFORMATION: CDR1 of humanized murine anti-human B7-2 heavy
      chain
<221> NAME/KEY: CDS
<222> LOCATION: (1)...(15)

<400> SEQUENCE: 9 gat tat gct ata cag                                                        15
Asp Tyr Ala Ile Gln
1               5

<210> SEQ ID NO 10
<211> LENGTH: 5
<212> TYPE: PRT
<213> ORGANISM: Artificial Sequence
<220> FEATURE:
<223> OTHER INFORMATION: CDR1 of humanized murine anti-human B7-2 heavy
      chain

<400> SEQUENCE: 10

Asp Tyr Ala Ile Gln
1               5

<210> SEQ ID NO 11
<211> LENGTH: 51
<212> TYPE: DNA
<213> ORGANISM: Artificial Sequence
<220> FEATURE:
<223> OTHER INFORMATION: CDR2 of humanized murine anti-human B7-2 heavy
      chain
<221> NAME/KEY: CDS
<222> LOCATION: (1)...(51)

<400> SEQUENCE: 11 gtt att aat att tac tat gat aat aca aac tac aac cag aag ttt aag           48
Val Ile Asn Ile Tyr Tyr Asp Asn Thr Asn Tyr Asn Gln Lys Phe Lys
1               5                   10                  15 ggc                                                                        51
Gly <210> SEQ ID NO 12
<211> LENGTH: 17
<212> TYPE: PRT
<213> ORGANISM: Artificial Sequence
<220> FEATURE:
<223> OTHER INFORMATION: CDR2 of humanized murine anti-human B7-2 heavy
      chain

<400> SEQUENCE: 12

Val Ile Asn Ile Tyr Tyr Asp Asn Thr Asn Tyr Asn Gln Lys Phe Lys
1               5                   10                  15

Gly
```

<210> SEQ ID NO 13
<211> LENGTH: 21
<212> TYPE: DNA
<213> ORGANISM: Artificial Sequence
<220> FEATURE:
<223> OTHER INFORMATION: CDR3 of humanized murine anti-human B7-2 heavy
      chain
<221> NAME/KEY: CDS
<222> LOCATION: (1)...(21)

<400> SEQUENCE: 13 gcg gcc tgg tat atg gac tac                                    21
Ala Ala Trp Tyr Met Asp Tyr
 1               5

<210> SEQ ID NO 14
<211> LENGTH: 7
<212> TYPE: PRT
<213> ORGANISM: Artificial Sequence
<220> FEATURE:
<223> OTHER INFORMATION: CDR3 of humanized murine anti-human B7-2 heavy
      chain

<400> SEQUENCE: 14

Ala Ala Trp Tyr Met Asp Tyr
 1               5

<210> SEQ ID NO 15
<211> LENGTH: 51
<212> TYPE: DNA
<213> ORGANISM: Artificial Sequence
<220> FEATURE:
<223> OTHER INFORMATION: CDR1 of humanized murine anti-human B7-2 light
      chain
<221> NAME/KEY: CDS
<222> LOCATION: (1)...(51)

<400> SEQUENCE: 15 aaa tcc agt cag agt ctg ctc aac agt aga acc cga gag aac tac ttg    48
Lys Ser Ser Gln Ser Leu Leu Asn Ser Arg Thr Arg Glu Asn Tyr Leu
 1               5                  10                  15 gct                                                                51
Ala

<210> SEQ ID NO 16
<211> LENGTH: 17
<212> TYPE: PRT
<213> ORGANISM: Artificial Sequence
<220> FEATURE:
<223> OTHER INFORMATION: CDR1 of humanized murine anti-human B7-2 light
      chain

<400> SEQUENCE: 16

Lys Ser Ser Gln Ser Leu Leu Asn Ser Arg Thr Arg Glu Asn Tyr Leu
 1               5                  10                  15

Ala

<210> SEQ ID NO 17
<211> LENGTH: 21
<212> TYPE: DNA
<213> ORGANISM: Artificial Sequence
<220> FEATURE:
<223> OTHER INFORMATION: CDR2 of humanized murine anti-human B7-2 light
      chain
<221> NAME/KEY: CDS
<222> LOCATION: (1)...(21)

```
-continued

<400> SEQUENCE: 17 tgg gca tcc act agg gaa tct                                          21
Trp Ala Ser Thr Arg Glu Ser
 1               5

<210> SEQ ID NO 18
<211> LENGTH: 7
<212> TYPE: PRT
<213> ORGANISM: Artificial Sequence
<220> FEATURE:
<223> OTHER INFORMATION: CDR2 of humanized murine anti-human B7-2 light
      chain

<400> SEQUENCE: 18

Trp Ala Ser Thr Arg Glu Ser
 1               5

<210> SEQ ID NO 19
<211> LENGTH: 24
<212> TYPE: DNA
<213> ORGANISM: Artificial Sequence
<220> FEATURE:
<223> OTHER INFORMATION: CDR3 of humanized murine anti-human B7-2 light
      chain
<221> NAME/KEY: CDS
<222> LOCATION: (1)...(24)

<400> SEQUENCE: 19 acg caa tct tat aat ctt tac acg                                      24
Thr Gln Ser Tyr Asn Leu Tyr Thr
 1               5

<210> SEQ ID NO 20
<211> LENGTH: 8
<212> TYPE: PRT
<213> ORGANISM: Artificial Sequence
<220> FEATURE:
<223> OTHER INFORMATION: CDR3 of humanized murine anti-human B7-2 light
      chain

<400> SEQUENCE: 20

Thr Gln Ser Tyr Asn Leu Tyr Thr
 1               5
```